United States Patent [19]
Owens et al.

[11] Patent Number: 5,851,784
[45] Date of Patent: Dec. 22, 1998

[54] HUMAN PHOSPHODIESTERASE TYPE IVC, AND ITS PRODUCTION AND USE

[75] Inventors: Raymond John Owens, Henley-on-Thames; Martin John Perry, Surrey; Simon Mark Lumb, Maidenhead, all of United Kingdom

[73] Assignee: Celltech Therapeutics, Limited, Berkshire, England

[21] Appl. No.: 577,492

[22] Filed: Dec. 22, 1995

[30]     Foreign Application Priority Data

Dec. 23, 1994 [GB]  United Kingdom .................... 9426227
Jun. 26, 1995 [GB]  United Kingdom .................... 9512996

[51] Int. Cl.$^6$ ...................................................... C12Q 1/44
[52] U.S. Cl. ...................... 435/19; 435/69.1; 435/320.1; 435/196; 435/325; 536/23.2; 536/23.5
[58] Field of Search ........................... 435/19, 69.1, 325, 435/320.1, 196; 536/23.2, 23.5

[56]         References Cited

FOREIGN PATENT DOCUMENTS

WO 91/09967   7/1991   WIPO.
WO 91/16457  10/1991   WIPO.

OTHER PUBLICATIONS

Engels et al (1995) FEBS Lett 358:305–310 "Molecular Cloning and Functional Expression in Yeast of a Human cAMP–specific . . . ".

Ulloa et al. (1988) FEBS Lett Z41:219–222 "Cyclic Nucleotide Phosphodiesterase Activity in Neurospora Crassa: Purification by Immunoaffinity . . . ".

Ausubel, F.M. et al. (ed), "Current Protocols in Molecular Biology", 1992, Wiley Interscience, vol. 1 and II.

Beavo, J.A. et al., "Primary Sequence of Cyclic Nucleotide Phosphodiesterase Isozymes and the Design of Selective Inhibitors", *Trends Pharmacol. Sci.*, 1990, 11, 150–155.

Belyauskey et al., "PCR–based cDNA library construction: general cDNA libraries at the level of a few cells", *Nucl. Acids Res.*, 1989, 17(8), 2919–2932.

Bolger, G. et al., "A Family of Human Phosphodiesterases Homologous to the dunce Learning and Memory Gene Product of *Drosophila melanogaster* Are Potential Targets for Antidepressant Drugs", *Mol. Cell Biol.*, 1993, 13(10), 6558–6571.

Cockett, M. et al., "The use of engineered E1A genes to transactivate the hCMV–MIE promoter in permanent CHO cell lines", *Nucl. Acids Res.*, 1991, 19(2), 319–325.

Conti, M. et al., "Characterization of a Hormone–Inducible, High Affinity Adenosine 3'–5'–Cyclic Monophosphate Phosphodiesterase from the Rat Sertoli Cell", *Biochemistry*, 1995, 34, 7979–7987.

Conti, M. et al., "Hormonal Regulation of Cyclic Nucleotide Phosphodiesterases", *Endocrine Rev.*, 1991, 12(3), 218–234.

Davis, R. et al., "Cloning and characterization of mammalian homologs of the *Drosophila* dunce+ gene", *Proc. Natl. Acad. Sci. USA*, 1989, 86, 3604–3608.

Dent, G. et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

Edwards et al., "Oligodeoxyribonucleotide ligation to single–stranded cDNAs: a new tool for cloning 5' ends of mRNAs and for constructing cDNA libraries by in vitro amplification", *Nucl. Acids Res.*, 1991, 19(19), 5227–5232.

Frohman et al., "Rapid production of full–length cDNAs from rare transcripts: Amplification using a single gene–specific oligonucleotide primer", *Proc. Natl. Acad. Sci. USA*, 1988, 85, 8998–9002.

Gillespie, P.G. et al., "Inhibition and Stimulation of Photoreceptor Phosphodiesterases by Dipyridamole and M&B 22, 948", *Mol. Pharmacol.*, 1989, 36, 773–781.

Harrison, S.A. et al., "Isolation and Characterization of Bovine Cardiac Muscle cGMP–Inhibited Phosphodiesterase: A Receptor for New Cardiotonic Drug", *Mol. Pharmacol.*, 1986, 29, 506–514.

Ito, H. et al., "Transformation of Intact Yeast Cells Treated with Alkali Cations", *J. Bacteriology*, 1983, 53(1), 163–168.

Jin, C. et al., "Characterization of the Structure of a Low $K_m$, Rolipram–sensitive cAMP Phosphodiesterase", *J. Biol. Chem.*, 1992, 267(26), 18929–18939.

Kaulen, P. et al., "Autoradiographic mapping of a selective cyclic adenosine monophosphate phosphodiesterase in rat brain with the antidepressant [$^3$H]rolipram", *Brain Res.*, 1989, 503, 229–245.

Kobilka, B. et al., "Delineation of the Intronless Nature of the Genes for the Human and Hamster β2–Adrenergic Receptor and Their Putative Promotor Regions", *J. Biol. Chem.*, 1987, 262(15), 7321–7327.

Kramer et al., "The gapped duplex DNA approach to oligonucleotide–directed mutation construction", *Nucl. Acids Res.*, 1984, 12(24), 9441–9456.

Laemmli, U.K., "Cleavage of Structural Proteins during the Assembly of the Head of Bacteriophage T4", *Nature*, 1970, 227, 680–685.

Livi et al., "Cloning and Expression of cDNA for a Human Low–$K_m$3 Rolipram–sensitive Cyclic AMP Phosphodiesterase", *Mol. Cell. Biol.*, 1990, 10, 2678–2686.

Londesborough, J. et al., "The Zinc–containing High $K_m$ Cyclic Nucleotide Phosphodiesterase of Bakers' Yeast", *J. Biol. Chem.*, 1983, 258(5), 2966–2972.

(List continued on next page.)

*Primary Examiner*—Rebecca E. Prouty
*Assistant Examiner*—Enrique D. Longton
*Attorney, Agent, or Firm*—Woodcock Washburn Kurtz Mackiewicz & Norris LLP

[57]         ABSTRACT

Recombinant human phosphodiesterase type IVC is described, and DNA coding for it. Particular conformers of the enzyme are identified, including a R- and S-rolipram stereoselective conformer which is obtainable by expression of human phosphodiesterase type IVC DNA in mammalian or insect cells. The recombinant enzyme may be used in a screen to select a compound capable of modulating the action of the enzyme, or as an immunogen to generate an antibody.

5 Claims, 15 Drawing Sheets

OTHER PUBLICATIONS

Mclaughlin, M. et al., "A Low-$K_m$, Rolipram–sensitive, cAMP–specific Phosphodiesterase from Human Brain", *J. Biol. Chem.*, 1993, 268(9), 6470–6476.

Sambrook et al., *Molecular Cloning*, 1989, Cold Spring Harbor Laboratory, New York.

Obernolte, R. et al., "The cDNA of a human lymphocyte cyclic–AMP phosphodiesterase (PDE IV) reveals a multigene family", *Gene*, 1993, 129, 239–247.

Peachell, P.T. et al., "Preliminary Identification and Role of Phosphodiesterase Isozymes in Human Basophils", *J. Immunol.*, 1992, 148(8), 2503–2510.

Pillai, R. et al., "Use of a yeast expression system for the isolation and analysis of drug–resistant mutants of a mammalian phosphodiesterase", *Proc. Natl. Acad. Sci. USA*, 1993, 90, 11970–11974.

Sanger F. et al., "DNA sequencing with chain–terminating inhibitors", *Proc. Natl. Acad. Sci. USA*, 1977, 74(12), 5463–5467.

Schmiechen, R. et al., "Close correlation between behavioural response and binding in vivo for inhibitors of the rolipram–sensitive phosphodiesterase", *Psychopharmacology*, 1990, 102, 17–20.

Schneider, H.H. et al., "Stereospecific Binding of the Antidepressant Rolipram to Brain Protein Structures", *Eur. J. Pharmacol.*, 1986, 127, 105–115.

Smith, B.J. et al., "A Phosphodiesterase Assay Using Alumina Microcolumns", *Analyt. Biochem.*, 1993, 214, 355–357.

Sommer, N. et al., "The antidepressant rolipram suppresses cytokine production and prevents autoimmune encephalomyelitis", *Nature Medicine*, 1995, 1(3), 244–248.

Souranta, K. et al., "Purification on Intact and Nicked Forms of a Zinc–containing, $Mg^{2+}$–dependent, Low $K_m$ Cyclic AMP Phosphodiesterase from Bakers' Yeast", *J. Biol. Chem.*, 1984, 259(11), 6964–6971.

Stephens, P. et al., "The construction of a highly efficient and versatile set of mammalian expression vectors", *Nucl. Acids Res.*, 1989, 17(17), 7110.

Swinnen, J.V. et al., "Molecular cloning of rat homologues of the *Drosophila melanogaster* dunce cAMP phosphodiesterase: Evidence for a family of genes", *Proc. Natl. Acad. Sci. USA*, 1989, 86, 5325–5329.

Swinnen, J.V. et al., "Properties and Hormonal Regulation of Two Structurally Related cAMP Phosphodiesterases from the Rat Sertoli Cell", *J. Biol. Chem.*, 1991, 266(27), 18370–18377.

Torphy, T. et al., "Coexpression of Human cAMP–specific Phosphodiesterase Activity and High Affinity Rolipram Binding in Yeast", *J. Biol. Chem.*, 1992, 267(3), 1798–1804.

Whittle, N. et al., "Expression in COS cells of a mouse—human chimaeric B72.3 antibody", *Protein Engineering*, 1987, 1(6), 499–505.

Wilson, M. et al., "Purification, characterization and analysis of rolipram inhibition of a human type–IVA cyclic AMP–specific phosphodiesterase expressed in yeast", *Biochem. J.*, 1994, 304, 407–415.

FIGURE 1A    SEQUENCE OF HUMAN PDE IVC cDNA.

```
              10              20              30              40
               *               *               *               *
    TTC GAC GTG ATC AGA CCC AAC TCA GAC CCG GTC ATA CTT GGA CCG AAT
    AAG CTG CAC TAG TCT GGG TTG AGT CTG GGC CAG TAT GAA CCT GGC TTA 50              60              70              80              90
      *               *               *               *               *
    GCT GCC AAA TCC CCC ACC TCT ACC CAG ATC TGA GCC TAC GCG GGG TGC
    CGA CGG TTT AGG GGG TGG AGA TGG GTC TAG ACT CGG ATG CGC CCC ACG 100             110             120             130             140
             *               *               *               *               *
    CGA CCC AGC TCG TGG ACG GGA ATA CGG TGA CCT TTG ACC CAA AAG TCT
    GCT GGG TCG AGC ACC TGC CCT TAT GCC ACT GGA AAC TGG GTT TTC AGA 150             160             170             180             190
               *               *               *               *               *
    TGG CCG GGA CCA GCC GGA CAC TGG CCC TCG GCC GGG AGC TCC GAG TCT
    ACC GGC CCT GGT CGG CCT GTG ACC GGG AGC CGG CCC TCG AGG CTC AGA 200             210             220             230             240
               *               *               *               *               *
    CAG GCG GTC CCG GTT GTC TTC CTG TCG GTG CCG CTT CCG CCT GCC CTT
    GTC CGC CAG GGC CAA CAG AAG GAC AGC CAC GGC GAA GGC GGA CGG GAA 250             260             270             280
               *               *               *               *
    CTT GAA AAC CCA CCC CCA GCT TTG ACC TGG AAA ATG GGC TCT CGT GTG
    GAA CTT TTG GGT GGG GGT CGA AAC TGG ACC TTT TAC CCG AGA GCA CAC 290             300             310             320             330
     *               *               *               *               *
    GGA GGA GGG CCC TGG ACC CTC AGT CCA GCC CTG GCC TGG GCC GGA TT ATG
    CCT CCT CCC GGG ACC TGG GAG TCA GGT CGG GAC CGG ACC CGG CCT AA TAC
                                                                        M>
                                                                    ___>

340             350             360             370             380
     *               *               *               *               *
    CAG GCT CCA GTC CCG CAC AGC CAG CGG CGC GAG TCC TTC CTG TAC CGC
    GTC CGA GGT CAG GGC GTG TCG GTC GCC GCG CTC AGG AAG GAC ATG GCG
     Q   A   P   V   P   H   S   Q   R   R   E   S   F   L   Y   R>
    ___a___a___a___a___a___a___a___a___a___a___a___a___a___a___a___>

390             400             410             420             430
           *               *               *               *               *
    TCA GAT AGC GAC TAT GAA CTC TCG CCC AAG GCC ATG TCT CGG AAC TCC
    AGT CTA TCG CTG ATA CTT GAG AGC GGG TTC CGG TAC AGA GCC TTG AGG
     S   D   S   D   Y   E   L   S   P   K   A   M   S   R   N   S>
    ___a___a___a___a___a___a___a___a___a___a___a___a___a___a___a___>
```

FIGURE 1B

```
             440              450              460              470              480
              *                *                *                *                *
    TCT GTG GCC AGC GAC CTA CAT GGA GAG GAC ATG ATT GTG ACG CCC TTT
    AGA CAC CGG TCG CTG GAT GTA CCT CTC CTG TAC TAA CAC TGC GGG AAA
     S   V   A   S   D   L   H   G   E   D   M   I   V   T   P   F>
     __a___a___a___a___a___a___a___a___a___a___a___a___a___a___a___>

490              500              510              520              530
              *                *                *                *                *
    GCC CAG GTC CTG GCC AGT CTG CGG ACC GTT CGG AGC AAC GTG GCG GCC
    CGG GTC CAG GAC CGG TCA GAC GCC TGG CAA GCC TCG TTG CAC CGC CGG
     A   Q   V   L   A   S   L   R   T   V   R   S   N   V   A   A>
     __a___a___a___a___a___a___a___a___a___a___a___a___a___a___a___>

540              550              560              570
                   *                *                *                *
        CTT GCC CGC CAG CAA TGC CTA GGA GCA GCC AAG CAG GGA CCC GTC GGA
        GAA CGG GCG GTC GTT ACG GAT CCT CGT CGG TTC GTC CCT GGG CAG CCT
         L   A   R   Q   Q   C   L   G   A   A   K   Q   G   P   V   G>
         __a___a___a___a___a___a___a___a___a___a___a___a___a___a___a___>

580              590              600              610              620
     *                *                *                *                *
    AAC CCT TCA TCC AGC AAT CAG CTC CCT CCT GCA GAG GAC ACG GGG CAG
    TTG GGA AGT AGG TCG TTA GTC GAG GGA GGA CGT CTC CTG TGC CCC GTC
     N   P   S   S   S   N   Q   L   P   P   A   E   D   T   G   Q>
     __a___a___a___a___a___a___a___a___a___a___a___a___a___a___a___>

630              640              650              660              670
              *                *                *                *                *
    AAG CTG GCA TTG GAG ACG CTA GAC GAG CTG GAC TGG TGC CTG GAT CAG
    TTC GAC CGT AAC CTC TGC GAT CTG CTC GAC CTG ACC ACG GAC CTA GTC
     K   L   A   L   E   T   L   D   E   L   D   W   C   L   D   Q>
     __a___a___a___a___a___a___a___a___a___a___a___a___a___a___a___>

680              690              700              710              720
              *                *                *                *                *
    TTG GAG ACG CTG CAG ACC CGG CAC TCG GTG GGG GAG ATG GCC TCC AAC
    AAC CTC TGC GAC GTC TGG GCC GTG AGC CAC CCC CTC TAC CGG AGG TTG
     L   E   T   L   Q   T   R   H   S   V   G   E   M   A   S   N>
     __a___a___a___a___a___a___a___a___a___a___a___a___a___a___a___>

730              740              750              760              770
              *                *                *                *                *
    AAG TTC AAG CGG ATC CTG AAC CGG GAG TTG ACC CAC CTG TCC GAA ACC
    TTC AAG TTC GCC TAG GAC TTG GCC CTC AAC TGG GTG GAC AGG CTT TGG
     K   F   K   R   I   L   N   R   E   L   T   H   L   S   E   T>
     __a___a___a___a___a___a___a___a___a___a___a___a___a___a___a___>

780              790              800              810
                   *                *                *                *
        AGC CGC TCC GGG AAC CAG GTG TCC GAG TAC ATC TCC CGG ACC TTC CTG
        TCG GCG AGG CCC TTG GTC CAC AGG CTC ATG TAG AGG GCC TGG AAG GAC
         S   R   S   G   N   Q   V   S   E   Y   I   S   R   T   F   L>
         __a___a___a___a___a___a___a___a___a___a___a___a___a___a___a___>
```

FIGURE 1C

```
          820            830             840           850            860
           *              *               *             *              *
     GAC CAG CAG ACC GAG GTG GAG CTG CCC AAG GTG ACC GCT GAG GAG GCC
     CTG GTC GTC TGG CTC CAC CTC GAC GGG TTC CAC TGG CGA CTC CTC CGG
      D   Q   Q   T   E   V   E   L   P   K   V   T   A   E   E   A>
     ___a___a___a___a___a___a___a___a___a___a___a___a___a___a___a___>

870            880             890           900            910
           *              *               *             *              *
     CCA CAG CCC ATG TCC CGG ATC AGT GGC CTA CAT GGG CTC TGC CAC AGT
     GGT GTC GGG TAC AGG GCC TAG TCA CCG GAT GTA CCC GAG ACG GTG TCA
      P   Q   P   M   S   R   I   S   G   L   H   G   L   C   H   S>
     ___a___a___a___a___a___a___a___a___a___a___a___a___a___a___a___>

920            930             940           950            960
           *              *               *             *              *
     GCC AGC CTC TCC TCA GCC ACT GTC CCA CGC TTT GGG GTC CAG ACT GAC
     CGG TCG GAG AGG AGT CGG TGA CAG GGT GCG AAA CCC CAG GTC TGA CTG
      A   S   L   S   S   A   T   V   P   R   F   G   V   Q   T   D>
     ___a___a___a___a___a___a___a___a___a___a___a___a___a___a___a___>

970            980             990           1000           1010
           *              *               *             *              *
     CAG GAG GAG CAA CTG GCC AAG GAG CTA GAA GAC ACC AAC AAG TGG GGA
     GTC CTC CTC GTT GAC CGG TTC CTC GAT CTT CTG TGG TTG TTC ACC CCT
      Q   E   E   Q   L   A   K   E   L   E   D   T   N   K   W   G>
     ___a___a___a___a___a___a___a___a___a___a___a___a___a___a___a___>

1020           1030            1040          1050
           *              *               *             *
     CTT GAT GTG TTC AAG GTG GCG GAG CTA AGT GGG AAC CAG CCC CTC ACA
     GAA CTA CAC AAG TTC CAC CGC CTC GAT TCA CCC TTG GTC GGG GAG TGT
      L   D   V   F   K   V   A   E   L   S   G   N   Q   P   L   T>
     ___a___a___a___a___a___a___a___a___a___a___a___a___a___a___a___>

1060           1070            1080          1090           1100
      *              *               *             *              *
     GCT ATC ATA TTC AGC ATT TTT CAG GAG CGG GAC CTG CTG AAG ACA TTC
     CGA TAG TAT AAG TCG TAA AAA GTC CTC GCC CTG GAC GAC TTC TGT AAG
      A   I   I   F   S   I   F   Q   E   R   D   L   L   K   T   F>
     ___a___a___a___a___a___a___a___a___a___a___a___a___a___a___a___>

1110           1120            1130          1140           1150
           *              *               *             *              *
     CAG ATC CCA GCA GAC ACA CTG GCC ACC TAC CTG CTG ATG CTG GAG GGT
     GTC TAG GGT CGT CTG TGT GAC CGG TGG ATG GAC GAC TAC GAC CTC CCA
      Q   I   P   A   D   T   L   A   T   Y   L   L   M   L   E   G>
     ___a___a___a___a___a___a___a___a___a___a___a___a___a___a___a___>

1160           1170            1180          1190           1200
           *              *               *             *              *
     CAC TAC CAC GCC AAT GTG GCC TAC CAC AAC AGC CTA CAT GCC GCC GAC
     GTG ATG GTG CGG TTA CAC CGG ATG GTG TTG TCG GAT GTA CGG CGG CTG
      H   Y   H   A   N   V   A   Y   H   N   S   L   H   A   A   D>
     ___a___a___a___a___a___a___a___a___a___a___a___a___a___a___a___>
```

FIGURE 1D

```
              1210             1220             1230             1240             1250
               *                *                *                *                *
      GTG GCC CAG TCC ACG CAT GTG CTG CTG GCT ACG CCC GCC CTC GAG GCT
      CAC CGG GTC AGG TGC GTA CAC GAC GAC CGA TGC GGG CGG GAG CTC CGA
       V   A   Q   S   T   H   V   L   L   A   T   P   A   L   E   A>
       __a___a___a___a___a___a___a___a___a___a___a___a___a___a___a___>

1260             1270             1280             1290
               *                *                *                *
      GTG TTC ACA GAC TTG GAA ATC CTG GCT GCC CTC TTT GCA AGC GCC ATC
      CAC AAG TGT CTG AAC CTT TAG GAC CGA CGG GAG AAA CGT TCG CGG TAG
       V   F   T   D   L   E   I   L   A   A   L   F   A   S   A   I>
       __a___a___a___a___a___a___a___a___a___a___a___a___a___a___a___>

1300             1310             1320             1330             1340
    *                *                *                *                *
  CAC GAC GTG GAC CAT CCT GGG GTC TCC AAC CAG TTT CTG ATT AAC ACC
  GTG CTG CAC CTG GTA GGA CCC CAG AGG TTG GTC AAA GAC TAA TTG TGG
   H   D   V   D   H   P   G   V   S   N   Q   F   L   I   N   T>
   __a___a___a___a___a___a___a___a___a___a___a___a___a___a___a___>

1350             1360             1370             1380             1390
          *                *                *                *                *
      AAC TCA GAG CTG GCG CTT ATG TAC AAC GAC GCC TCG GTG CTG GAG AAC
      TTG AGT CTC GAC CGC GAA TAC ATG TTG CTG CGG AGC CAC GAC CTC TTG
       N   S   E   L   A   L   M   Y   N   D   A   S   V   L   E   N>
       __a___a___a___a___a___a___a___a___a___a___a___a___a___a___a___>

1400             1410             1420             1430             1440
              *                *                *                *                *
      CAT CAC CTG GCT GTG GGC TTC AAG CTG CTG CAG GCA GAG AAC TGC GAT
      GTA GTG GAC CGA CAC CCG AAG TTC GAC GAC GTC CGT CTC TTG ACG CTA
       H   H   L   A   V   G   F   K   L   L   Q   A   E   N   C   D>
       __a___a___a___a___a___a___a___a___a___a___a___a___a___a___a___>

1450             1460             1470             1480             1490
              *                *                *                *                *
      ATC TTC CAG AAC CTC AGC GCC AAG CAG CGA CTG AGT CTG CGC AGG ATG
      TAG AAG GTC TTG GAG TCG CGG TTC GTC GCT GAC TCA GAC GCG TCC TAC
       I   F   Q   N   L   S   A   K   Q   R   L   S   L   R   R   M>
       __a___a___a___a___a___a___a___a___a___a___a___a___a___a___a___>

1500             1510             1520             1530
                  *                *                *                *
          GTC ATT GAC ATG GTG CTG GCC ACA GAC ATG TCC AAA CAC ATG AAC CTC
          CAG TAA CTG TAC CAC GAC CGG TGT CTG TAC AGG TTT GTG TAC TTG GAG
           V   I   D   M   V   L   A   T   D   M   S   K   H   M   N   L>
           __a___a___a___a___a___a___a___a___a___a___a___a___a___a___a___>

1540           1550             1560             1570             1580
    *              *                *                *                *
  CTG GCC GAC CTC AAG ACC ATG GTG GAG ACC AAG AAG GTG ACA AGC CTC
  GAC CGG CTG GAG TTC TGG TAC CAC CTC TGG TTC TTC CAC TGT TCG GAG
   L   A   D   L   K   T   M   V   E   T   K   K   V   T   S   L>
   __a___a___a___a___a___a___a___a___a___a___a___a___a___a___a___>
```

FIGURE 1E

```
         1590          1600          1610          1620          1630
          *             *             *             *             *
    GGT GTC CTC CTC CTG GAC AAC TAT TCC GAC CGA ATC CAG GTC TTG CAG
    CCA CAG GAG GAG GAC CTG TTG ATA AGG CTG GCT TAG GTC CAG AAC GTC
     G   V   L   L   L   D   N   Y   S   D   R   I   Q   V   L   Q>
    ___a___a___a___a___a___a___a___a___a___a___a___a___a___a___a___>

1640          1650          1660          1670          1680
          *             *             *             *             *
    AAC CTG GTG CAC TGT GCT GAT CTG AGC AAC CCC ACC AAG CCG CTG CCC
    TTG GAC CAC GTG ACA CGA CTA GAC TCG TTG GGG TGG TTC GGC GAC GGG
     N   L   V   H   C   A   D   L   S   N   P   T   K   P   L   P>
    ___a___a___a___a___a___a___a___a___a___a___a___a___a___a___a___>

1690          1700          1710          1720          1730
          *             *             *             *             *
    CTG TAC CGC CAG TGG ACG GAC CGC ATC ATG GCC GAG TTC TTC CAG CAG
    GAC ATG GCG GTC ACC TGC CTG GCG TAG TAC CGG CTC AAG AAG GTC GTC
     L   Y   R   Q   W   T   D   R   I   M   A   E   F   F   Q   Q>
    ___a___a___a___a___a___a___a___a___a___a___a___a___a___a___a___>

1740          1750          1760          1770
               *             *             *             *
    GGA GAC CGC GAG CGT GAG TCG GGC CTG GAC ATC AGT CCC ATG TGT GAC
    CCT CTG GCG CTC GCA CTC AGC CCG GAC CTG TAG TCA GGG TAC ACA CTG
     G   D   R   E   R   E   S   G   L   D   I   S   P   M   C   D>
    ___a___a___a___a___a___a___a___a___a___a___a___a___a___a___a___>

1780          1790          1800          1810          1820
 *             *             *             *             *
AAG CAT ACG GCC TCA GTG GAG AAG TCC CAG GTG GGT TTC ATT GAC TAC
TTC GTA TGC CGG AGT CAC CTC TTC AGG GTC CAC CCA AAG TAA CTG ATG
 K   H   T   A   S   V   E   K   S   Q   V   G   F   I   D   Y>
___a___a___a___a___a___a___a___a___a___a___a___a___a___a___a___>

1830          1840          1850          1860          1870
          *             *             *             *             *
    ATT GCT CAC CCA CTG TGG GAG ACT TGG GCT GAC CTG GTC CAC CCA GAT
    TAA CGA GTG GGT GAC ACC CTC TGA ACC CGA CTG GAC CAG GTG GGT CTA
     I   A   H   P   L   W   E   T   W   A   D   L   V   H   P   D>
    ___a___a___a___a___a___a___a___a___a___a___a___a___a___a___a___>

1880          1890          1900          1910          1920
          *             *             *             *             *
    GCA CAG GAC CTG CTG GAC ACG CTG GAG GAC AAT CGA GAG TGG TAC CAG
    CGT GTC CTG GAC GAC CTG TGC GAC CTC CTG TTA GCT CTC ACC ATG GTC
     A   Q   D   L   L   D   T   L   E   D   N   R   E   W   Y   Q>
    ___a___a___a___a___a___a___a___a___a___a___a___a___a___a___a___>

1930          1940          1950          1960          1970
          *             *             *             *             *
    AGC AAG ATC CCC CGA AGT CCC TCA GAC CTC ACC AAC CCC GAG CGG GAC
    TCG TTC TAG GGG GCT TCA GGG AGT CTG GAG TGG TTG GGG CTC GCC CTG
     S   K   I   P   R   S   P   S   D   L   T   N   P   E   R   D>
    ___a___a___a___a___a___a___a___a___a___a___a___a___a___a___a___>
```

FIGURE 1F

```
            1980          1990          2000          2010
             *             *             *             *
    GGG CCT GAC AGA TTC CAG TTT GAA CTG ACT CTG GAG GAG GCA GAG GAA
    CCC GGA CTG TCT AAG GTC AAA CTT GAC TGA GAC CTC CTC CGT CTC CTT
     G   P   D   R   F   Q   F   E   L   T   L   E   E   A   E   E>
      a   a   a   a   a   a   a   a   a   a   a   a   a   a   a   >

2020          2030          2040          2050          2060
   *             *             *             *             *
  GAG GAT GAG GAG GAA GAA GAG GAG GGG GAA GAG ACA GCT TTA GCC AAA
  CTC CTA CTC CTC CTT CTT CTC CTC CCC CTT CTC TGT CGA AAT CGG TTT
   E   D   E   E   E   E   E   E   G   E   E   T   A   L   A   K>
    a   a   a   a   a   a   a   a   a   a   a   a   a   a   a   >

2070          2080          2090          2100          2110
     *             *             *             *             *
    GAG GCC TTG GAG TTG CCT GAC ACT GAA CTC CTG TCC CCT GAA GCC GGC
    CTC CGG AAC CTC AAC GGA CTG TGA CTT GAG GAC AGG GGA CTT CGG CCG
     E   A   L   E   L   P   D   T   E   L   L   S   P   E   A   G>
      a   a   a   a   a   a   a   a   a   a   a   a   a   a   a   >

2120          2130          2140          2150          2160
         *             *             *             *             *
        CCA GCC CCT GGG GAC TTA CCC CTC GAC AAC CAG AGG ACT TAG GAA TTC
        GGT CGG GGA CCC CTG AAT GGG GAG CTG TTG GTC TCC TGA ATC CTT AAG
         P   A   P   G   D   L   P   L   D   N   Q   R   T   *   E   F>
          a   a   a   a   a   a   a   a   a   a   a   a   a   a   a   >
```

FIGURE 2A  ALIGNMENTS OF HUMAN PDE IV AMINO ACID SEQUENCES.

```
GENE A      MEPPTVPSERSLSLSLPGPREGQATLKPPPQHLWRQPRTPIRIQQFGY

GENE A      SDSAERAERERQPHRPIERADAMDTSDRPGLRTTRMSWPSSFHGTGTGSGGAGGGSSRRFEAENGTSA
GENE B2                                    MKEHGGTFSSTGISGGSGDSAMDSLQPLQPNYM...........
GENE D                                                              MMHVNNFPFRRHSWICFDVDNGTSA

GENE A      GRSPLDPMTSPSPGLVLHAGAATSQRRESFLYRSDSDYDMSPKTMSRNSSVTSEAHAEDLIVTPFAQV
GENE B2     ................MQAPVPHSQRRESFLYRSDSDYELSPKAMSRNSSVASDLHGEDMIVTPFAQV
GENE C                      MQAPVPHSQRRESFLYRSDSDYELSPKAMSRNSSVASDLHGEDMIVTPFAQV
GENE D      GRSPLDPMTSPGSGLLILQANFVHSQRRESFLYRSDSDYDLSPKSMSRNSSIASDIHGDDLIVTPFAQV

GENE A      LASLRSVRSNFSLLTNVPVP.SNKRSPLGGPT.PVCKATLSEETCQQLARETLEELDWCLEQLETMQT
GENE B2     ..................................PVCLFA..EESYQKLAMETLEELDWCLDQLETIQT
GENE C      LASLRTVRSNVAALARQQCLGAAKQGPVGNPSSSNQ.LPPAEDTGQKLALETLDELDWCLDQLETLQT
GENE D      LASLRTVRNNFAALTNLQDRAPSKRSPMCNQPSIN.KATITEEAYQKLASETLEELDWCLDQLETLQT

GENE A      YRSVSEMASHKFKRMLNRELTHLSEMSRSGNQVSEYISTTFLDKQNEVEIPSPTMKEREKQQAPRPRP
GENE B2     YRSVSEMASNKFKRMLNRELTHLSEMSRSGNQVSEVISNTFLDKQNDVEIPSPTQKDREK....KKKQ
GENE C      RHSVGEMASNKFKRILNRELTHLSETSRSGNQVSEYISRTFLDQQTEVELP........KVTAEEAPQ
GENE D      RHSVSEMASNKFKRMLNRELTHLSEMSRSGNQVSEFISNTFLDKQHEVEIPSPTQKEKEK....KKR.
```

FIGURE 2B

```
GENE A   SPPPPPVPH LQPMSQITGLKKLMHSNSLNNSNIPRFGVKTDQEELLAQELENLNKWGLNIFCVSDYA
GENE B2  Q........ ..LMTQISGVKKLMHSSSLNNTSISRFGVNTENEDHLAKELEDLNKWGLNIFNVAGYS
GENE C   ......... ...PMSRISGLHGLCHSASLSSATVPRFGVQTDQEEQLAKELEDTNKWGLDVFKVAELS
GENE D   ......... ...PMSQISGVKKLMHSSSLTNSSIPRFGVKTEQEDVLAKELEDVNKWGLHVFRIAELS

GENE A   GGRSLTCIMYMIFQERDLLKKFRIPVDTMVTYMLTLEDHYHADVAYHNSLHAADVLQSTHVLLATPAL
GENE B2  HNRPLTCIMYAIFQERDLLKTFRISSDTFITYMMTLEDHYHSDVAYHNSLHAADVAQSTHVLLSTPAL
GENE C   GNQPLTAIIFSIFQERDLLKTFQIPADTLATYLLMLEGHYHANVAYHNSLHAADVAQSTHVLLATPAL
GENE D   GNRPLTVIMHTIFQERDLLKTFKIPVDTLITYLMTLEDHYHADVAYHNNIHAADVVQSTHVLLSTPAL

GENE A   DAVFTDLEILAALFAAAIHDVDHPGVSNQFLINTNSELALMYNDESVLENHHLAVGFKLLQEENCDIF
GENE B2  DAVFTDLEILAAIFAAAIHDVDHPGVSNQFLINTNSELALMYNDESVLENHHLAVGFKLLQEEHCDIF
GENE C   EAVFTDLEILAALFASAIHDVDHPGVSNQFLINTNSELALMYNDASVLENHHLAVGFKLLQAENCDIF
GENE D   EAVFTDLEILAAIFASAIHDVDHPGVSNQFLINTNSELALMYNDSSVLENHHLAVGFKLLQEENCDIF

GENE A   QNLSKRQRQSLRKMVIDMVLATDMSKHMTLLADLKTMVETKKVTSSGVLLLDNYSDRIQVLRNMVHCA
GENE B2  MNLTKKQRQTLRKMVIDMVLATDMSKHMSLLADLKTMVETKKVTSSGVLLLDNYTDRIQVLRNMVHCA
GENE C   QNLSAKQRLSLRRMVIDMVLATDMSKHMNLLADLKTMVETKKVTSLGVLLLDNYSDRIQVLQNLVHCA
GENE D   QNLTKKQRQSLRKMVIDIVLATDMSKHMNLLADLKTMVETKKVTSSGVLLLDNYSDRIQVLQNMVHCA

GENE A   DLSNPTKPLELYRQWTDRIMAEFFQQGDRERERGMEISPMCDKHTASVEKSQVGFIDYIVHPLWETWA
GENE B2  DLSNPTKSLELYRQWTDRIMEEFFQQGDKERERGMEISPMCDKHTASVEKSQVGFIDYIVHPLWETWA
GENE C   DLSNPTKPLPLYRQWTDRIMAEFFQQGDREREESGLDISPMCDKHTASVEKSQVGFIDYIAHPLWETWA
GENE D   DLSNPTKPLQLYRQWTDRIMEEFFRQGDRERERGMEISPMCDKHNASVEKSQVGFIDYIVHPLWETWA
```

FIGURE 2C

```
GENE A   DLVHPDAQEILDTLEDNRDWYYSAIRQSPSPPPEEESRGPGHPPLPDKFQFELTLEEEEISRAQ
GENE B2  DLVQPDAQDILDTLEDNRNWYQSMIPQSPSPPLDEQNRDCQG..LMEKFQFELTLDEEDSEGPEKEG
GENE C   DLVHPDAQDLLDTLEDNREWYQSKIPRSPSDLTNPERDGPDR......FQFELTLEEAEEEDEEEE
GENE D   DLVHPDAQDILDTLEDNREWYQSTIPQSPSPAPDDPEEGRQGQTG..KFQFELTLEEDGESDTEKDS

GENE A   IRCTAQEALTEQGLSGVEEALDATIAWEASPAQESLEVMAQEASLEAELEAVYLTQQAQSTGSEPVA
GENE B2  EGHSYFSSTKTLCVIDPENRDSLGETDIDIATEDKSPVDT*
GENE C   EGEETALAKEALELPDTELLSPEAGPAPGDLPLDNQRT*
GENE D   GSQVEEDTSCSDSKTLCTQDSESTEI PLDEQVEEEAVGEEEESQPEACVIDDRSPDT*

GENE A   PDEFSNREEFVVAVSHSSPSALALQSPLLPAWRTLSVSEHAPGLPGLPSTAAEVEAQREHQAAKRACS

GENE A   ACAGTFGEDTSALPAPGGGGSGGDPT*
```

FIGURE 3  ALIGNMENT OF HUMAN AND RAT PDE IVC AMINO ACID SEQUENCES.

```
huC.pep     ETL EEL DWC LDQ LET LQT RHS VGE MAS NKF KRI LNR ELT HLS ETS RSG
ratC.pep    ETL EEL DWC LeQ LET LQT RrS VGE MAS NKF KRm LNR ELT HLS ETS RSG> huC.pep     NQV SEY ISR TFL DQQ TEV ELF Kvt aee apq pms ris     gLH GLC HS
ratC.pep    NQV SEY ISq TFL DQQ aEV ELP a............lLr ksC Ht> huC.pep     SAT VPR FGV QTD QEE QLA KEL EDT NKW GLD VFK VAE LSG NQP LTA IIF
ratC.pep    tAa iPR FGV QTD QEE QLA KEL EDT NKW GLD VFK VAE LSG NrP LTA vIF> huC.pep     SIF QER DLL KTF QIP ADT LAT YLL MLE GHY HAN VAY HNS LHA ADV AQS
ratC.pep    rvl QER DLL KTF QIP ADT Llr YLL tLE GHY HsN VAY HNS iHA ADV vQS> huC.pep     THV LLA TPA LEA VFT DLE ILA ALF ASA IHD VDH PGV SNQ FLI NTN SEL
ratC.pep    aHV LLg TPA LEA VFT DLE vLA AiF ACA IHD VDH PGV SNQ FLI NTN SEL> huC.pep     ALM YND ASV LEN HHL AVG FKL LQA ENC DIF QNL SAK QRL SLR RMV IDM
ratC.pep    ALM YND sSV LEN HHL AVG FKL LQg ENC DIF QNL StK QkL SLR RMV IDM> huC.pep     VLA TDM SKH MNL LAD LKT MVE TKK VTS LGV LLL DNY SDR IQV LQN LVH
ratC.pep    VLA TDM SKH MsL LAD LKT MVE TKK VTS LGV LLL DNY SDR IQV LQs LVH> huC.pep     CAD LSN PTK PLP LYR QWT DRI MAE FFQ QGD RER ESG LDI SPM CDK HTA
ratC.pep    CAD LSN PaK PLP LYR QWT eRI MAE FFQ QGD RER ESG LDI SPM CDK HTA> huC.pep     SVE KSQ VGF IDY IAH PLW ETW ADL VHP DAQ DLL DTL EDN REW YQS KIP
ratC.pep    SVE KSQ VGF IDY IAH PLW ETW ADL VHP DAQ eLL DTL EDN REW YQS rvP> huC.pep     RSP SDL TNP ERD GPD RFQ FEL TLE EAE EED EEE GEE TAL AKE ALE
ratC.pep    ........ P ERD GPD RFQ FEL TLE EAE EED EEE huC.pep     LPD TEL LSP EAG PAP GDL PLD NQR T
```

```
GCT GTC CAG AAA AGG TCC CGC GCA GTC GGC GCT CGG TCC AGC
CGA CAG GTC TTT TCC AGG GCG CGT CAG CCG CGA GCC AGG TCG
 A   V   Q   K   R   S   R   A   V   G   A   R   S  S>
___a___a___a___a___a___a___a___a___a___a___a___a___a___>

CTC CAC GCA GTC CTG GCG ATG CAG GGC CCC CCC GCG CCC GCC
GAG GTG CGT CAG GAC CGC TAC GTC CCG GGG GGG CGC GGG CGG
 L   H   A   V   L   A   M   Q   G   P   P   A   P  A>
___a___a___a___a___a___a___a___a___a___a___a___a___a___>

100
                           *
CCG GTC CCC GGG CCC GGC TCC CCT CGG GGA TCC CCG CGC GGC
GGC CAG GGG CCC GGG CCG AGG GGA GCC CCT AGG GGC GCG CCG
 P   V   P   G   P   G   S   P   R   G   S   P   R  G>
___a___a___a___a___a___a___a___a___a___a___a___a___a___>

TCC CCC GGG CTC TTC AGG AAG CTT TTG GTG AAT CAG AGC ATC
AGG GGG CCC GAG AAG TCC TTC GAA AAC CAC TTA GTC TCG TAG
 S   P   G   L   F   R   K   L   L   V   N   Q   S  I>
___a___a___a___a___a___a___a___a___a___a___a___a___a___>

200
                                           *
CGC CTG CAG CGG CGC TTC ACG GTG GCC CAT CCG CTG TGC TTT
GCG GAC GTC GCC GCG AAG TGC CAC CGG GTA GGC GAC ACG AAA
 R   L   Q   R   R   F   T   V   A   H   P   L   C  F>
___a___a___a___a___a___a___a___a___a___a___a___a___a___>

GAC CTG GAA AAT GGG CTC TCG TGT GGG AGG AGG GCC CTG GAC
CTG GAC CTT TTA CCC GAG AGC ACA CCC TCC TCC CGG GAC CTG
 D   L   E   N   G   L   S   C   G   R   R   A   L  D>
___a___a___a___a___a___a___a___a___a___a___a___a___a___>

CCT CAG TCC AGC CCT GGC CTG GGC CGG ATT ATG CAG GCT CCA
GGA GTC AGG TCG GGA CCG GAC CCG GCC TAA TAC GTC CGA GGT
 P   Q   S   S   P   G   L   G   R   I   M   Q   A  P>
___a___a___a___a___a___a___a___a___a___a___a___a___a___>

300
       *
GTC CCG CAC AGC CAG CGG CGC GAG TCC TTC CTG TAC CGC TCA
CAG GGC GTG TCG GTC GCC GCG CTC AGG AAG GAC ATG GCG AGT
 V   P   H   S   Q   R   R   E   S   F   L   Y   R  S>
___a___a___a___a___a___a___a___a___a___a___a___a___a___>
```

Figure 7 Sequence of alternative 5' end of human PDE IVC mRNA. The sequence that differs from the one shown in figure 1 is underlined.

HUMAN PHOSPHODIESTERASE TYPE IVC, AND ITS PRODUCTION AND USE

This invention relates to human phosphodiesterase type IVC and its production, to conformers, analogues and fragments thereof, to nucleic acids encoding the enzyme, and to the use of the enzyme in drug screening and as an immunogen.

The role of cyclic AMP (cAMP) as a second messenger is well recognised. It is responsible for transducing the effects of a variety of extracellular signals, including hormones and neurotransmitters. The level of intracellular cAMP is regulated through both its synthesis by adenyl cyclases and degradation by cyclic nucleotide phosphodiesterases (PDE).

PDEs form a family of at least seven enzyme isotypes (I–VII) which differ in their affinity for cAMP and/or cGMP, subcellular localisation and regulation (Beavo J. A. and Reifsnyder D. H. (1990) Trends Pharmacol. Sci. 11 150–155; Conti M. et al. (1991) Endocrine Rev. 12 218–234). In the same way that receptors controlling the synthesis of cAMP have offered opportunities for developing selective therapeutic agents, the PDEs may afford similar possibilities for drug development. In fact the clinical effects of a number of drugs can be rationalised on the basis of their selectivity for a particular PDE isotype. For example, the cardiotonic drugs milrinone and zaprinast are PDE III and PDE V inhibitors respectively. (Harrison S. A. et al (1986) Mol. Pharmacol. 29 506–514; Gillespie P. G. and Beavo J. (1989) Mol. Pharmacol. 36 773–781). The anti-depressant drug, rolipram functions as a selective PDE IV inhibitor. (Schneider H. H. et al. (1986) Eur. J. Pharmacol. 127 105–115.).

The availability of PDE isotype selective inhibitors has enabled the role of PDEs in a variety of cell types to be investigated. In particular it has been established that PDE IV controls the breakdown of cAMP in many inflammatory cells, for example basophils (Peachell P. T. et al. (1992) J. Immunol. 148 2503–2510 ) and eosinophils (Dent G. et al. (1991) Br. J. Pharmacol. 103 1339–1346) and that inhibition of this isotype is associated with the inhibition of cell activation. Consequently PDE IV inhibitors are currently being developed as potential anti-inflammatory drugs, particularly for the treatment of asthma in which the non-selective PDE inhibitor, theophylline, has been shown to have a therapeutic effect.

The application of molecular cloning to the study of PDEs has revealed that for each isotype there may be one or more isoforms. For PDE IV, it is has been shown that there are four isoforms (A, B, C and D) each coded for by a separate gene in both rodents (Swinnen J. V. et al. (1989) Proc. Natl. Acad. Sci. USA 86 5325–5329) and man (Bolger G. et al. (1993) Mol. Cell Biol. 13 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al.. 1989; Bolger et al. 1993; Obernolte R. et al (1993) Gene 129 239–247, ibid) and the high degree of sequence conservation amongst isoforms of different species. To pursue the development of isoform selective inhibitors requires the availability of each enzyme type for evaluation.

To date full length cDNAs for human PDE IVA, B and D (Bolger et al. 1993 ibid; Obernolte. etal. 1993 ibid; Mclaughlin M. et al. (1993) J. Biol. Chem. 268 6470–6476) and rat PDE IVA, B and D (Davis R. et al. (1989) Proc. Natl. Acad. Sci. USA 86 3604–3608; Swinnen J. V. et al. (1991) J. Biol. Chem. 266 18370–18377), have been reported, enabling functional recombinant enzymes to be produced by expression of the cDNAs in an appropriate host cell. These cDNAs have been isolated by conventional hybridisation methods. However using this approach, only partial cDNAs for both human and rat PDE IVC have been obtained. (Bolger etal. ibid. 1993 and Swinnen et al. ibid. 1989 and International Patent Specification No. WO 91/16457.). These sequences are insufficient for producing a functional enzyme.

Although it might be expected that human PDE IVC cDNA could be fairly readily obtained by using conventional hybridisation approaches, this has not been the case, possibly due to the lower abundance of its mRNAs compared to the other three isoforms (Bolger et al 1993 ibid). To overcome this problem we have devised a novel strategy for cloning the human PDE IVC mRNA (based on the approach to primer design and described more particularly in the experimental section hereinafter) which has allowed us to obtain a functional enzyme by expression of the cDNA in mammalian, yeast and insect cells. This has enabled the properties of this enzyme to be compared to the A, B and D isoforms in terms of substrate kinetics and inhibition by PDE IV selective inhibitors.

Thus according to one aspect of the invention we provide an isolated nucleic acid molecule which encodes a human phosphodiesterase type IVC[PDE IVC].

Particular nucleic acids according to the invention comprise the nucleotide sequence depicted in FIGS. 1A to 1F hereinafter, (SEQ ID No: 31) analogues and fragments thereof. The term "analogue" is meant to include all those DNA molecules which have the sequence shown in FIGS. 1A to 1F but in which one or more nucleotides has been changed or one or more extra nucleotides is present. The term "fragment" is meant to include DNA molecules again having the sequence depicted in FIGS. 1A to 1F but in which one or more nucleotides has been deleted. The term is also meant to include analogues in which one or more nucleotides has been deleted. It will be immediately understood that for an analogue or fragment to qualify as a DNA molecule according to the invention it must be able to encode a functional (catalytically active) PDE IVC. The DNA may comprise genomic DNA, cDNA or a combination of both.

The nucleic acids according to the invention may be obtained from any suitable human source using an appropriate probe as described herein. Once obtained, a nucleic acid may be modified by standard molecular biology and/or chemistry techniques, e.g. by use of oligonucleotide directed mutagenesis or oligonucleotide directed synthesis techniques, enzymatic cleavage or enzymatic filling in of gapped oligonucleotides, to obtain nucleic acid analogues or fragments of the invention. Alternatively, the nucleic acid may itself be used as a probe to obtain complementary copies of genomic DNA, CDNA or RNA from other human sources, using conventional genomic, CDNA and/or PCR cloning techniques.

The PDE IVC nucleic acid according to the invention may be of use in therapy, for example where it is desired to modify the production of PDE IVC in vivo and the invention extends to such a use.

Knowledge of the nucleic acid according to the invention also provides the ability to regulate its activity in vivo by for example the use of antisense DNA or RNA. Thus, according to a further aspect of the invention we provide an antisense DNA or an antisense RNA of a gene coding for human phosphodiesterase type IVC, said gene containing nucleic acid comprising the nucleotide sequence of FIGS. 1A to 1F herein, or an analogue or fragment thereof.

The antisense DNA or RNA can be produced using conventional means, by standard molecular biology techniques and/or by chemical synthesis. If desired, the antisense DNA and antisense RNA may be chemically modified so as to prevent degradation in vivo or to facilitate passage through a cell membrane, and/or a substance capable of inactivating mRNA, for example ribosyme, may be linked thereto, and the invention extends to such constructs.

The antisense DNA or RNA may be of use in the treatment of diseases or disorders in which the over- or unregulated production of PDE IVC has been implicated, for example in inflammatory diseases.

In particular, however, the nucleic acids according to the invention may be used to produce human PDE IVC or an analogue or fragment thereof. Thus, according to a further aspect of the invention we provide a recombinant human phospodiesterase type IVC or an analogue or fragment thereof.

The PDE IVC may in particular be an isolated enzyme, for example a partially purified cell-free enzyme, such as part of a cell supernatant or a purified enzyme substantially free of cellular or extraneous protein or other material. Analogues or fragments of the enzyme according to the invention are those proteins which still retain the human PDE IVC catalytic activity but which have one or more additional, fewer, or different amino acids to the naturally occurring enzyme.

A particularly useful protein according to the invention comprises the human PDE IVC amino acid sequence depicted in FIGS. 1A to 1F or 2A–2C hereinafter (SEQ ID No: 32) and analogues and fragments thereof. A particular analogue is that comprising the amino acid sequence depicted in FIGS. 1A to 1F together with the additional 5' amino acid sequence depicted in FIG. 7 hereinafter (SEQ ID No: 37).

Unexpectedly, we have found that is is possible to obtain the human PDE IVC enzyme of the invention in more than one catalytically active conformation, as demonstrated in the experimental section below, and the invention thus extends to all conformers of the isolated enzyme, analogues and fragments thereof. The ability of the PDE IVC sequence of the invention to direct the expression of different conformers of the enzyme which are distinguishable by their sensitivity to selective inhibitors in a catalytic assay was not predicted by the results for the expression of PDE IVA, B and D reported by others (e.g. Bolger et al, (1993) ibid; Livi et al, (1990) Mol. Cell. Biol. 10, 2678–2686; Maclaughin et al (1992) ibid). The usefulness of such distinct conformers is that they enable the potency of novel inhibitors to be evaluated in the same assay format, namely inhibition of cAMP hydrolysis.

A particularly useful conformer according to the invention is that obtainable by expression of the PDE IVC enzyme in mammalian cells as described hereinafter. This form of the enzyme is characterised by its ability in an in vitro assay to distinguish between the R- and S- enantiomers of the known PDE IV inhibitor rolipram. Such a conformer, which maintains a stereo-selectivity for inhibition by R- and S- rolipram in vitro, and is distinct from other non-selective conformers, for example as obtainable by expression of the enzyme in yeast, is particularly advantageous for use to evaluate the properties of PDE IV inhibitors in an in vitro screen as described hereinafter.

As used herein the term "conformer" means any form of the PDE IVC enzyme as distinguished by its catalytic response to inhibitors, and extends for example to forms of the enzyme which may incorporate a post-translation modification, for example a phosphorylated form and other modified forms of the enzyme.

The PDE IVC protein, analogues or fragments thereof may be obtained by expression of the corresponding nucleic acids using appropriate expression vectors in any suitable procaryotic or eucaryotic host cell, using methods well known in the art (see for example "Current Protocols in Molecular Biology", Vol. I and 11, Ansubel, F. M. et al (ed), Wiley Interscience, 1992), and the methods described in the experimental section hereinafter. Where desired the enzyme may be isolated from cell lysates and optionally purified using conventional techniques for example by ion-exchange and other chromatographic techniques.

Particular conformers may be obtained from different cell types. Thus the R- and S-rolipram stereoselective conformer according to the invention may be obtained for example by expression of the PDE IVC enzyme in mammalian cells, such as CHO or COS cells. Alternatively, a conformer of this type may be obtained by expression of the PDE IVC enzyme in insect cells, e.g. Sf9 cells. A non-selective conformer as described herein may be obtained from yeast cells.

The PDE IVC proteins according to the invention may be used to screen for agents which modulate the action of the protein, for example phosphodiesterase inhibitors, especially PDE IVC isoform selective inhibitors, for use in medicine, and the invention is to be understood to extend to such a use, and to screens containing the PDE IVC protein of the invention.

Thus according to a further aspect of the invention we provide a method for selecting a compound which modulates the action of human phosphodiesterase type IVC which comprises contacting a test compound with a recombinant human phosphodiesterase type IVC in a test system containing a substrate for the enzyme and monitoring any modulation of the action of the enzyme due to the presence of the test compound.

In this aspect of the invention the recombinant PDE IVC enzyme may be an isolated enzyme, in particular a R- and S-rolipram stereoselective conformer as described herein. Alternatively, the enzyme may be expressed during the operation of the assay from a cell, particularly a mammalian or insect cell, transformed with the PDE IVC nucleic acid according to the invention. Test compounds for use in this aspect of the invention may be synthetic or naturally occurring.

Such a screen may be especially useful for selecting a PDE IVC isoform selective inhibitor for use in medicine, and the invention extends to inhibitors selected in this way. Use of the R- and S-rolipram stereo-selective conformer of the invention as the target enzyme in the screen can be expected to provide for the selection of inhibitors with advantageous properties since based on the results described hereinafter, this form of the enzyme may be assumed to more closely model the native enzyme than non-selective conformers, for example those produced in a host such as yeast. Inhibitors selected in this way may be of use in the prophylaxis and treatment of inflammatory diseases, for example in the prophylaxis and treatment of asthma, especially inflamed lung associated with asthma. The inhibitors may be formulated for use as pharmaceutical compositions, together with one or more pharmaceutically acceptable carriers, excipients or diluents in accordance with conventional practice.

Antibodies may also be generated to one or more epitopes of the proteins according to the invention using conventional immunization and recombinant DNA techniques and the invention extends to the use of a human PDE IVC according to the invention as an immunogen.

Thus, for example polyclonal antibodies may be obtained from the sera of animals immunised with a phosphodiesterase according to the invention or an analogue or fragment thereof. Any suitable host, for example BALB/c mice where it is desired to obtain a mouse polyclonal antibody, may be injected with the immunogen, the serum collected and the antibody recovered therefrom. Monoclonal antibodies may be obtained from hybridomas derived from the spleen cells of an animal immunised as just discussed and fused to an appropriate "immortal" B-tumour cell. In each instance, the antibody may be recovered from either the serum or the hybridoma by making use of standard purification and or concentration techniques, for example by chromatography, using for example Protein A or by other affinity chromatography employing a phosphodiesterase of the invention or an analogue or fragment thereof.

Once a cell line, for example a hybridoma, expressing an antibody has been obtained it is possible to clone therefrom the cDNA and to identify the variable region genes encoding the desired antibody, including the sequences encoding the CDRs. From here, other engineered antibodies may be obtained by preparing one or more replicable expression vectors containing at least the DNA sequence encoding the variable domain of the antibody heavy or light chain and optionally other DNA sequences encoding remaining portions of the heavy and/or light chains as desired, and transforming an appropriate cell line, e.g. a non-producing myeloma cell line, such as a mouse NSO line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International pic sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91/09967.

Polyclonal, monoclonal and engineered antibodies obtained in the above general ways and which are capable of binding recombinant human PDE IVC, especially a R- and S-rolipram stereoselective conformer thereof form a further feature of the invention. Such antibodies may be of use, for example, in analytical tests, PDE IVC purification procedures and the like.

The invention is now described in the Examples below, with reference to the following Figures.

SUMMARY OF FIGURES

FIGS. 1A to 1F: DNA sequence (SEQ ID No; 31) and amino acid sequence (SEQ ID No: 32) of human PDE IVC.

FIGS. 2A to 2C: Alignment of human PDE IV amino acid sequences. GENE A=SEQ ID No: 33, GENE B2=SEQ ID No: 34, GENE C=SEQ ID No: 32 GENE D=SEQ ID No: 35.

FIG. 3: Alignment of human (SEQ ID No: 40) and rat (SEQ ID No: 38) PDE IV amino acid sequences.

FIG. 7: DNA sequence (SEQ ID No: 36) and amino acid sequence (SEQ ID No: 37) of alternative 5' end of human PDE IVC.

Figure 4:
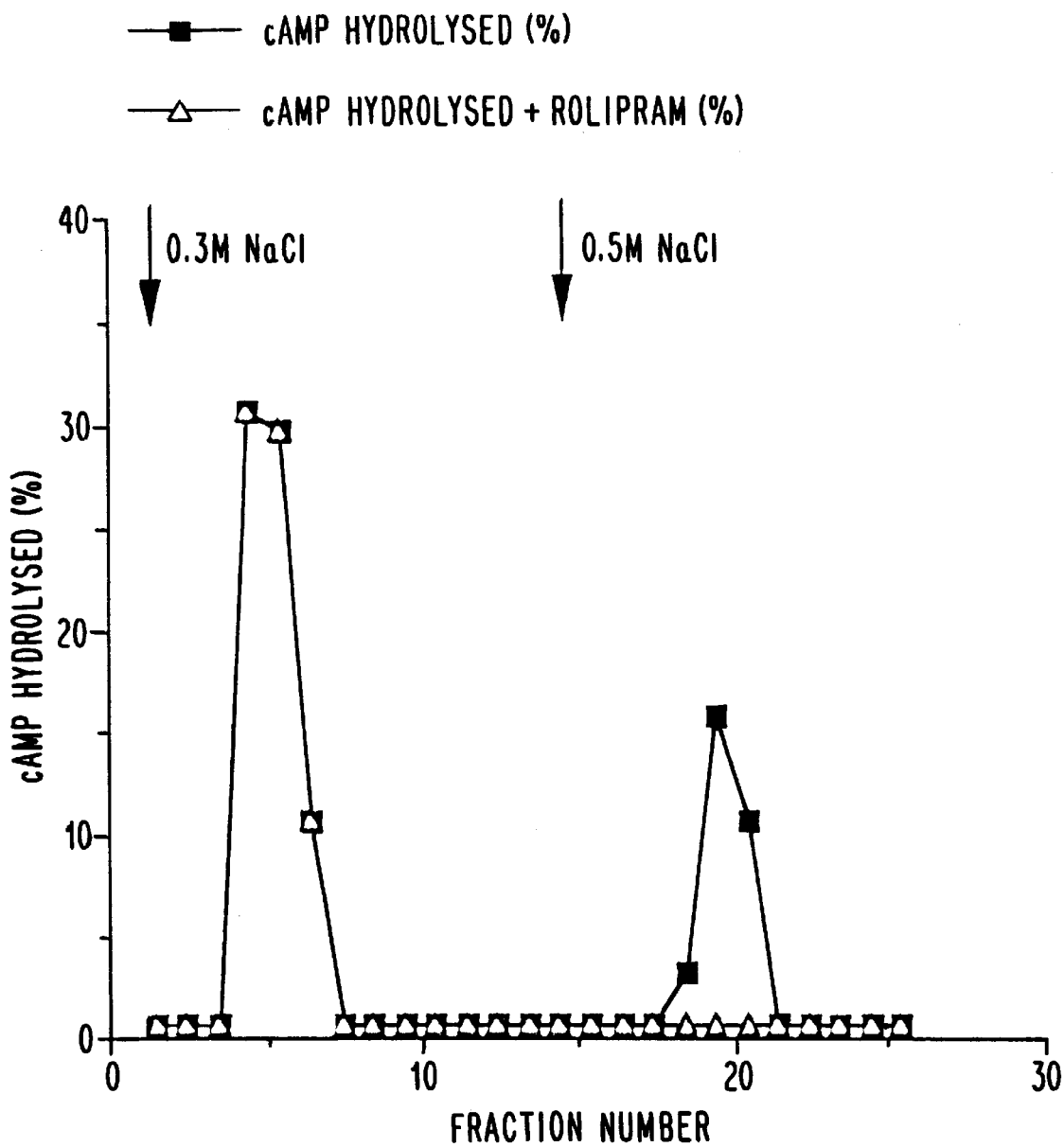
FIG. 4: Separation of recombinant PI)F IVC from yeast PDE activity by monoQ Sepharose ion-exchange chromatography.

EXPERIMENTAL PROCEDURES.

RT.PCR analysis.

To identify a source of gene C mRNA, a number of cell lines were assayed for isoform mRNAs by reverse transcription coupled to polymerase chain reaction (RT.PCR). Total RNA was prepared using RNAzol (Biogenesis) and polyA+ mRNA selected by affinity chromatography using oligodT cellulose. 50 ng of first strand cDNA prepared by reverse transcriptase was amplified with the following pairs of gene specific primers for 40 cycles using the conditions, 94° C. 1 min, 55° C. 1 min, 72° C. 3min.

Gene A

Foward primer R3090. SEQ ID No:1
5' GATCGGATCCGCGGCTGCCATCCACGATGTGGATCACCCTGGGG 3'
Reverse primer R4148. SEQ ID No:2
5' TTTTTGGATCCGGGATCAGGTAGGGTCTC 3'

Gene B

Forward primer R4138. SEQ ID No:3
5' TTTTTAAGCTTCAGCTCATGACCCAGATAAG 3'
Reverse primer R4143. SEQ ID No:4
5' TTTGGATCCGATAGAAGTTCATCTCCAC 3'

Gene C

Forward primer R5130. SEQ ID No:5
5' TTTTTGAATTCGATATCTTCCAGAACCTCAGCGC 3'

-continued

Reverse primer R5192. SEQ ID No:6
5' TTTTTGAATTCCTAAGCCTCTGGTTGTCGAG 3'

Gene D

Forward primer R5205. SEQ ID No:7
5' TTTTTGAATTCAGAGTTGTCTGGTAACCGGC 3'
Reverse primer R5206. SEQ ID No:8
5' TTTTGAATTCGTTACGTGTCAGGAGACG 3'
NB restriction sites in the primers are underlined.

Isolation of gene C cDNA.

A partial PDE IVC CDNA clone was isolated from U87 cell mRNA using RT.PCR. A 5' PCR primer was designed based on the prediction that a short stretch of amino acid sequence towards the amino terminus of gene C would be identical to that of the A,B,D isoforms previously cloned. A mixture of oligonucleotides were synthesised that would be expected to hybridise to the DNA sequence encoding this segment of the gene. Two features of the primer design advantageously minimise the number of different sequences required. Firstly, codon usage was based on the sequence of the other three PDEIV isoforms. Secondly, only the last five codons were varied. An ATG was added to the 5' end of the PDE sequence to enable any amplified sequences to be directly expressed. A Hind3 restriction enzyme cloning site was also incorporated into the primers. The target amino acid sequence and oligonucleotides are shown below:

R5857. SEQ ID No:9                                SEQ ID NO:39
5'
            M   E   T   L   E   E   L   D   W   C
   CGCGCGAAGCTTATGGAGACGCTGGAGGAGCTAGACTGGTGT3'
                              AT G

The 3' PCR primer was R5192 shown above and incorporated an EcoR1 site for cloning. Amplification was carried out using the conditions described above. A 1500 bp PCR product was obtained and sub-cloned into the commercially available vector pSP73 to produce the plasmid pDEU1. 12 independent clones were sequenced on both strands and identified as gene C by reference to the published partial sequence.

To isolate the 5' terminus of PDE IVC and the initiating methionine residue the protocol of a commercial PCR based strategy (5' Amplifinder™ Race, Clontech) was followed. The RACE method (rapid amplification of cDNA ends) was first described by Frohman et. al. [(1988) Proc. Natl. Acad. Sci. USA 85 8998–9002] and Belyauskey et al. [(1989) Nucl.Acids Res. 17 2919–2932]. The Clontech method is a modified version of that described by Edwards et al [(1991) Nucl. Acids Res. 19 5227–5232], involving single-stranded ligation of a nucleotide anchor to the 3' end of the first-strand CDNA, thus avoiding homopolymeric tailing.

As with the partial PDE IVC clone (PDEU1) described above, first strand CDNA was synthesised from 2 ug of U87 cell mRNA using R6333 as the priming oligonucleotide.

R6331. SEQ ID No:10
5'-TTTCTCGAGGGTTTCGGACAGGTGGGTCAACTCCCG-3'
R6332. SEQ ID No:11
5'-TTTCTCGAGGCCACTGATCCGGGACATGGGCTG-3'
R6333. SEQ ID No:12
5'-TTTCTCGAGCCACTTGTTGGTGTCTTCTAGCTC-3'

The primary PCR reaction consisted of 5 ul of single-stranded ligation mix, 5U Taq polymerase, 2 ul dimethylsulphoxide (DMSO), 250 uM deoxyribonucleotide triphosphates (dNTPs), 0.2 uM anchor primer, 0.2 uM oligonucleotide R6332 and H$_2$O to a total volume of 50 ul.

The reaction was amplified for 35 cycles under the following parameters, 95° C./1 min, 65° C./1 min, 72° C./1 min. The secondary PCR reaction consisted of, 2 ul of a 1:10 dilution of the primary PCR mixture, 5U Taq polymerase 2 ul DMSO, 250 uM dNTPS, 0.2 uM anchor primer, 0.2 uM oligonucleotide R6331 and H$_2$O to a total volume of 50 ul. Amplification was carried under the same parameters as in the primary PCR reaction.

The products of the secondary PCR reaction were digested with the restriction enzymes EcoR1 and BamH1, the sites which are contained within the ligated anchor and within the PDE IVC sequence respectively. The fragments were cloned into EcoR1/BamH1 digested psP65 vector (Promega), recombinant colonies were identified by PCR screening, sequenced on both strands and confirmed as PDE IVC. The resulting plasmid containing a 470 bp fragment was named pDER2. Translation of the nucleotide sequence identified a methionine residue at position 336 bp unfortunately, the reading frame remained open and it could not be confirmed as the initiating methionine. The clone did however contain all of the Upstream Conserved Region 1 (UCR 1) recently described (Bolger et al. ibid 1993).

The RACE method was repeated again this time using oligonucleotides derived from the new 5' sequence described above.

The primary and secondary PCR reactions were carried out under the same conditions as described above using oligonucleotides R6532 and R6533 respectively.

R6532. SEQ ID No:13
5'-TTTGGATCCGGCCAGGACCTGGGCAAAGGGCG-3'
R6533. SEQ ID No:14
5'-TTTGGATCCGGCCTTGGGCGAGAGTTCATAGTCGC-3'

The products of the secondary PCR reaction were restricted with EcoR1 (anchor site) and BamH1 (also contained within the gene specific oligo R6533) and cloned into commercially available pSP65. Recombinant colonies were identified by PCR analysis and plasmid DNA was isolated and sequenced on both strands. Sequence analysis revealed that all four clones were identical, however, two of the four clones had extended 5' sequence. When translated all of the clones contained a 5' termination codon in the same position. The first initiating methionine residue downstream corresponded to the methionine residue described in PDER2.

To construct a catalytically active full length PDE IVC gene, the internal BamH1 site was used to add the new 5' sequence to the partial clone. pDEU1 and pDER2 were digested with BamH1 and EcoR1 to release two fragments of 1424 & 470bp respectively. The eukaryotic expression vector pEE7hcmv (Stephens P. and Cockett M. [(1989) Nucl.Acids Res. 17 7110] was digested with EcoR1. A three-way ligation was carried out and transformants were screened by PCR to determine the orientation of the inserts. Plasmid DNA was purified and sequenced on both strands. The plasmid was named pDEU7. The Hind 3-EcoR1 fragment containing the full length gene C from pDEU7 was inserted into the yeast expression vector pYES (InVitrogen) to produce the vector pDEU8

Isolation of CDNA clones for gene A

A partial cDNA for gene A was isolated by PCR from a CDNA library prepared from PMA stimulated U937 cells using published sequence information (Livi G. et al. (1990) ibid)). Subsequently a conserved region probe form this cDNA was used to isolate a full length cDNA clone from a human frontal cortex cDNA library by hybridisation and washing at moderate stringency (final wash 2×SSC, 0.5% SDS at 60° C.). The sequence of this clone is identical to that of Bolger et al. ibid. (1993) with following minor differences G>A at 724bp=met to ile change, G>A at 1238 bp silent change.

The full length gene for PDE IVA was introduced into pEE7 and pYES vectors for expression in COS and yeast cells respectively.

Northern blot analysis

The distribution of PDE IV isoform mRNAs in different human tissues was analysed by northern blotting. Human multiple tissue northern blots purchased from Clontech were hybridised with isoform specific probes generated by PCR from the 3' non-translated region of each gene. Either HL-60 genomic DNA (probes A and C) or a cDNA library prepared from eosinophil enriched mRNA (probes B and D) were used as templates for PCR amplification with the following pairs of primers and the conditions described above.

Gene A.
Forward primer R6069. SEQ ID No:15
5' TTTTAAGCTTGACCTCTGTCCCTGTTCCCCTCC 3'
Reverse primer R6095. SEQ ID No:16
5' TTTTTGGATCCGGCTGGAAGACTGAGCCTGGACC 3'

Gene B.
Forward primer R607. SEQ ID No:17
5' TTTTTGGATCCGCATGCCAGCTATGTGGTAGGG 3'
Reverse primer R6072. SEQ ID No.18
5' TTTTTGAATTCGGCAGACAAAGGGACAAGTGAGAAG 3'

Gene C.
Forward primer R6039. SEQ ID No:19
5' TTTTTAAGCTTCAGCCCTGCGTGAACTGCAGG 3'
Reverse primer R6040. SEQ ID No:20
5' TTTTTGAATTCGACTCAAGAGTGACCACTGGAG 3'

Gene D.
Forward primer R6073. SEQ ID No:21
5' TTTTTAAGCTTCCAAAGTGCATGTCACATGCCAC 3'
Reverse primer R6074. SEQ ID No.22
5' TTTTTGAATTCGAGGTCAGTGCAGCTCACTGAAC 3'

Gene-specific probes were radiolabelled with $^{32}$P.dCTP using random priming. RNA blots were hybridised for 1 h at 65° C. in Expresshy™ (Clontech) and washed for 40 min at room temp. in 2×SSC, 0.05% SDS and then for 40 min at 65° C. in 0.1×SSC, 0.1% SDS. Blots were exposed to X-ray film with intensifying screens at −70° C. for up to 7 days.

Construction of PDE IVA and PDE IVC deletion mutants.

Deletion analyses of rat PDE IVD (Jin C. (1992) J.Biol.Chem. 267 18929–18939 ) and PDE IVB (Pillai R. et al. (1993) Proc.Natl.Acad.Sci.USA 90 11970–11974) have defined the minimum enzyme sequence required for catalytic activity. Corresponding deletions were made to both human PDE IV A and C enzymes and the activity of the resulting enzymes evaluated following transient expression in COS cells.

PDE IVA PCR was used to construct a plasmid (pDEFC18) containing the first 129 bp (Met1 to Ile 43) of the PDE IVA gene. In addition a 3' BamH1 restriction enzyme site was introduced into the sequence. The PCR primers were as follows:

R5836. forward primer. SEQ ID No:23
5' TTTTAAGCTTCCACCATGGACCCCCGACCGTC 3'
R5840. reverse primer. SEQ ID No:24
5' TTTTGCGCTGCGGATCCGGATGGG 3'

A mutant deleted to the beginning of the catalytic domain (Ile43-Gln 330; Bolger et al. 1993 ibid) was produced by PCR using the following primers:

R 5839. forward primer.  SEQ ID No: 25
5' TTTTTGGATCCAGCCCATGTCCCAAATCAC 3'

R 5882. reverse primer.  SEQ ID No: 26
5' TTTTTGAATTCCTCGAGCACCGACTCATCG 3'

The PCR fragment was restricted with BamH1 and EcoR1 and cloned into the plasmid, pDEFC18 described above to produce the vector pDEFC23. Following sequencing this vector was restricted with Hind3 and Xho1 and inserted into Hind3/Xba1 restricted pEE7 together with a Xho1/Xba1 fragment corresponding to the remaining 3' portion of gene A. The final plasmid was designated pDEFC24.

PDE IVC The mutant enzyme deleted to the position in PDEIVC corresponding to the PDE IVA deletion (Met180) was produced by PCR using the following primers:

26272. forward primer.  SEQ ID No: 27
5' GCGCGCAAGCTTGCCACCATGTCCCGGATCAGTGGCCTAC 3'

26273. reverse primer.  SEQ ID No. 28
5' GAACACAGCCTCGAGGGCGGGCGTAGCC 3'

The PCR amplified fragment was restricted with Hind3 and Xho1 and inserted into psp73 to produce the plasmid pDEU9. Following sequencing of the insert this plasmid was then restricted with Hind3 and Xho1 and ligated to a Xho1/EcoR1 fragment from pDEU7 containing the remaining 3' portion of gene C and inserted into Hind3/EcoR1 restricted pEE7. The resulting plasmid was designated pDEU10.

Expression systems

Recombinant PDE IV enzymes were produced in COS cells by transient expression as described by Whittle N. et al. ([1987) Prot. Engineering 1 499–505]. Briefly 5×10$^5$ cells/ml were transfected with 10 ug of plasmid. After 3 days in culture cells were washed with PBS and lysed by brief sonciation in 50mM TES buffer, pH 7.6, (N tris [hydroxymethyl]methyl) 2-aminoethane sulphonic acid containing proteases inhibitors (50 uM leupeptin, 1 uM pepstatin, 1 um phenylmethylsulphonylfluoride, 2uM benzamidine). The cell homogenate was centrifuged ×12000 g for 10 min. and assayed for PDE IV activity.

For expression of full length PDE IVA and C cDNAs in Chinese hamster ovary cells (CHO) L761 cells, the plasmids, pDEFC17 and pDEU7 were introduced into the cells by calcium phosphate precipitation (Cockett M. et al. (1991) Nucl. Acids Res 19 319–325).

For expression of PDE IVA and C in yeast cells, the two genes were inserted into the vector pYES (InVitrogen) as either Hind3/Xba1 (gene A) or EcoR1 (gene C) fragments isolated from pDEFC17 and pDEU7 vectors respectively. The resulting plasmids were designated as pDEFC 32 and pDEU8 respectively.Yeast cells (B7542: alpha, ura-3,trp1+, Leu2delta, pep4: His3, prBdelta 1.6R can 1, gal) were transformed with pDEFC32 and pDEU8 vectors using the lithium acetate method (Ito H. et al. (1983) J.Bacteriol. 53

163–168). Ura3 positive prototrophs were isolated and grown at 30° C. to an $OD_{600}$=1.0 in minimal media containing 2% glucose and 50 mg/ml leucine. Cells were recovered by centrifugation, washed and resuspended at $OD_{600}$=0.5 in minimal media containing 2% galactose to induce PDE IV expression. At an $OD_{600}$=1.0 cells were harvested, washed and broken in TES buffer plus proteases (see above) by milling with glass beads (425–600 um) at 4° C. The homogenate was clarified by centrifugation at 100,000 g for 30 mins at 4° C. For large scale production of PDE IV enzymes, yeast cells were grown to 1.8L scale in a fed-batch fermenter PDE expression was routinely induced by addition of galactose at $OD_{600}$=30–40 and cells harvested approximately 48 hours later.

For expression of PDE IVC in insect cells, the gene was inserted into the transfer vector, pVL 1392 (In Vitrogen), as an EcoR1 fragment isolated from pDEU7. The resulting plasmid was designated as pDEU16. Sf9 cells were cotransfected with purified AcNPV linear DNA (Pharmingen) and pDEU16 transfer vector as described by Summers and Smith (1987) Texas Agricultural Experimental Station Bulletin No. 1555. Growth, plaque purification and titration of viruses were carried out using standard procedures. For production of protein, cells were grown in spinner flasks to $2\times10^6$/ml, infected with a multiplicity of infection of 10 and harvested after 60h.

Enzyme assays

Enzyme reactions were carried out at pH 7.6 in 50 mM TES buffer containing 10mM $MgCl_2$, 3',5' cAMP (0.1 uM $^3$H-labelled 0.74–1.1 TBq/mmol) 5'AMP (2.5 uM $^{14}$C, 1.85–2.2 GBq/mmol) for 30 min at 30° C. Sufficient enzyme preparation was added to hydrolyse not more than 20% of substrate under these conditions. For Km determinations, unlabelled cAMP was added to achieve substrate concentrations in the range 0.1–20 uM. Reactions were stopped by rapid inactivation of enzyme by addition of trifluoroacetic acid to a final concentration of 1%. Substrate and product of reaction were separated as described by Smith et aL [(1993) Analyt. Biochem. 214 355–357] and the [$^3$H] 5'AMP product analysed by scintillation counting.Correction for losses of [$^3$H] 5'AMP during separation was made by reference to [14C] 5' AMP included in the reaction mixture.

Isolation of human beta 2 adrenergic receptor gene.

The human beta 2 adrenergic receptor gene (Kobilka B. et al. (1987) J. Biol. Chem. 262 7321–7327) was isolated from HL-60 cells genomic DNA by PCR using the following primers:

R5690. forward primer. SEQ ID No: 29
5' GCGCGCAAGCTTCGCTTACCTGCCAGACTGCGC 3'

R 5691. reverse primer. SEQ ID No: 30
5' GCGCGCGAATTCTCTGTTTAGTGTTCTGTTGGG 3'

The PCR fragment was restricted with Hind3 and EcoR1 and inserted into pEE6 Bgl2 neo vector (Stephens P. and Cockett M. (1989) Nucl. Acids Res. 17 71 10) for expression in mammalian cells. The plasmid was named pRO144.

Measurement of intracellular cAMP in isoproterenol stimulated CHO cells co-tranfected with beta 2 adreneraic receptor and PDE IV A or C.

Transfected cells were harvested with non-enzymatic cell dissociation reagent (Sigma) washed three times and re-suspended in Dulbecco's phosphate buffered saline containing 0.1% BSA and 0.1% glucose (DPBS+). The celss were incubated with 10 uM inhibitor (or solvent control, 0.1% DMSO) in DPBS+for 10 min at 37° C. The cell suspension was stimulated with isoproterenol (0.001–1 uM) for 2 min. The cells were pelleted at 12000 g and resuspended in 400 uL of boiling assay buffer (DuPont cAMP measurement kit). The samples were heated in a boiling water bath for 10 min and frozen before being assayed for cAMP using a commercial cAMP radioimmunoassay (DuPont).

SDS-PAGE and Western blotting.

SDS-PAGE was carried out according to Laemmli (1970) Nature 227 680–685 using 10% (w/v) acrylamide gels. For Western blotting proteins were transferred to nitrocellulose and probed with a rabbit polyclonal antiserum raised to a C-terminal PDE IVC peptide.

Results

Cloning and sequence analysis of human PDE IVC.

A series of PCR amplification steps was used to assemble a putative full length version of the human PDE IVC mRNA The composite sequence of the three overlapping cDNAs that were isolated is shown in FIG. 1A to 1F, SEQ ID No: 31. The sequence contains an ORF of 1818 bp in length which predicts a 605 amino acid protein with a calculated molecular mass of approximately 66.5 kD. Evidence was also obtained for a second PDE IVC mRNA which diverges from the first sequence at position 259bp (FIGS. 1A to 1F) This represents a point of alternative exon splicing in both human PDE IVA and D (Bolger et al. ibid 1993). It is predicted therefore that the primary transcript of human PDE IVC gene in common with other PDE IV genes is differentially processed to produce at least two mRNAs that differ in their 5' sequence.

FIGS. 2A to 2C shows an alignment of the human PDE IVC primary amino acid sequence (SEQ ID No: 32) with sequences of the three other cloned human PDE IVs, GENE A (SEQ ID No: 33), GENE B2 (SEQ ID No: 34) and GENE D (SEQ ID No: 35). The PDE IVC is highly homologous to the PDE IVA, B and D sequences particularly in the two upstream conserved regions (UCR1 and UCR2, as defined by Bolger et al. (1993), ibid) and central catalytic region, where amino acid identity is >/=90%. Outside these homologous domains, the sequence in common with the other PDE IVs is isoform specific particularly C terminal of the catalytic domain. Comparison of the human PDE IVC with the partial rat PDE IVC sequence (SEQ ID NO: 38) shows that these isoform-specific regions have been relatively conserved between isoforms of different species. Thus overall the sequence of human PDE IVC is probably more homolgous to the same isoform in different species than different isoforms of the same species (FIG. 3), SEQ ID NO: 40 SEQ ID No: 36. This apparent conservation of PDE IV isoforms implies conservation of functional significance.

The sequence of the alternative 5' end for human PDE IVC is shown in FIG. 7, SEQ ID NO: 36 and SEQ ID NO: 37. This sequence contains an ATG at position 63 bp which may represent the start site of this mRNA. However, since the reading frame remains open upstream of this ATG, this cannot be conclusively assigned as the initiation site.

Expression In COS cells and evaluation of catalytic activity.

Recombinant human PDE IVC was produced by transient expression in COS cells. The product was recovered in the soluble fraction of the lysed cells (×12000 g supernatant) and migrated with an apparent molecular weight of approximately 80 kD on SDS PAGE as revealed by Western blotting using a human PDE IVC specific polyclonal rabbit antiserum. The PDE IV activity expressed in COS cells was markedly inhibited by the PDE IV selective inhibitors, rolipram and denbufylline and also by the broad spectrum PDE inhibitor IBMX (Table 1). This inhibition profile of PDE IVC was compared to that of PDE IVA also produced by transient expression in COS cells. Most interestingly, the PDE IVC enzyme showed significantly greater sensitivity to both rolipram and denbufylline compared to PDE IVA (Table 1). In additon the PDE IVC enzyme demonstrated stereoselectivity for the R-form of rolipram, whereas the PDE IVA did not. It has been reported that the $IC_{50}$'s for rolipram inhibition of PDE IVs A, B and D are very similar at around 200–500 nM (Livi etal. (1990); Maclaughlin et al. (1993); Bolger et al. (1993) ibid.) Thus the PDE IVC enzyme obtained from COS cells appears to exhibit distinct pharmacological properties from the other PDE IV isoforms, which can be exploited in the development of isoform selective inhibitors.

TABLE 1

| Enzyme<br>Inhibitor | PDE IVA | PDE IVC |
|---|---|---|
| | (IC50 nM) | |
| Rolipram (racemate) | 205 | 32 |
| R-rolipram | 292 | 21 |
| S-rolipram | 145 | 317 |
| Denbufylline | 2295 | 61 |
| IBMX | 10549 | 2164 | mRNA tissue and cell distribution.

The distribution of the PDE IVC mRNA(s) was investigated by both Northern blotting and reverse-transcription coupled to PCR (RT.PCR).

The results are summarised in Tables 2 and 3. The Northern blotting data indicate that PDE IV isoform mRNAs are widely distributed in human tissues with isoform C mRNA least abundant. Each isoform produces at least two mRNA species of distinct size (A=4.5 kb, B=4 &5 kb, C=6.0 kb, D=7.5–8.0 kb). Brain and skeletal muscle appear to have the highest levels of all isoform mRNAs.

The results of RT.PCR using the human gene primers to detect isoform mRNAs in both human tissue culture cells and rat tissues confirms that PDE IV mRNAs are widely distributed though the apparent levels of each isoform mRNA varies. Gene C mRNA appears to be more abundant than A,B, or D in cells derived from dorsal root ganglia and testes in rat. This latter result is consistent with data reported previously by Swinnen et al. (1989) ibid. Interestingly, treatment of cell lines with $bt_2$ cAMP leads to an increase in some but not all PDE IV isoform mRNAs. Thus in the human cells HL-60 and SKN.SH, levels of C and D but not A and B are elevated.

TABLE 2

| TISSUE | A | B | C | D |
|---|---|---|---|---|
| Heart | ++ | ++ | ND | + |
| Brain | +++ | ++++ | ++ | ++++ |
| Placenta | + | + | ND | + |
| Lung | ++ | ++ | ND | ++++ |
| Liver | + | + | ND | + |
| Skeletal Muscle | ++++ | ++++ | +++ | +++++ |
| Kidney | ++ | ++ | ND | ++++ |
| Pancreas | ++ | ND | ND | (+/−) |
| Spleen | + | ++ | ND | + |
| Thymus | + | + | ND | ++ |
| Prostate | + | ++ | ND | +++ |
| Testes | ++ | + | ND | (+/−) |
| Ovary | + | + | + | + |
| Small Intestine | + | + | + | ++ |

TABLE 2-continued

| TISSUE | A | B | C | D |
|---|---|---|---|---|
| Colon | + | + | ND | ++ |
| PBL | ++ | +++ | ND | ++++ |

ND = Not Detected

TABLE 3

| CELLS | A | B | C | D |
|---|---|---|---|---|
| U937 | − | + | +/− | + |
| Jurkat | + | − | − | + |
| T98G | + | + | +/− | + |
| U87 | + | + | + | + |
| SKNSH | + | + | + | + |
| HL60 | + | + | −/+ | + |
| Neutrophils | − | + | + | + |
| B50 (rat) | + | + | − | not determined |
| NG115 (rat) | + | + | − | not determined |
| TISSUES (rat)* | A | B | C | D |
| Liver | + | − | + | + |
| Testes | + | + | ++ | + |
| Brain | + | + | +/− | + |
| Heart | − | − | − | − |
| Kidney | − | − | − | − |
| DRG | + | + | + | − |
| Bt₂ CAMP stimulated CELLS | A | B | C | D |
| HL60 0h | + | + | −/+ | + |
| HL60 2h | + | + | + | ++ |
| HL60 6h | + | + | + | ++ |
| SKNSH 0h | − | − | − | ++ |
| SKNSH 2h | − | − | + | ++ |
| SKNSH 6h | − | − | + | not determined |

*Rat tissue PCR carried out using human primers.

Expression In yeast and CHO cells.

Both PDE IVC and PDE IVA were expressed in yeast and CHO cells. The CHO cell lysates were analysed for PDE activity and inhibition by rolipram. $IC_{50}$'s of 43 and 287 nM for C and A respectively were obtained which are consistent with results for the enzymes produced in COS cells (Table 1).

Yeast express two endogenous PDE activities (Londesborough J. and Souranta K. (1983) J. Biol. Chem. 258 2966–2972; Souranta K. and Londesborough J. (1984) J.Biol.Chem. 259 6964–6971). Therefore, yeast cell lysates were fractionated by ion-exchange chromatography to separate the recombinant PDE IV activity from the host cell enzymes (FIG. 4). The sensitivity of the fraction enriched for PDE IVC activity to inhibition by rolipram was evaluated. Unexpectedly, this enzyme demonstrated limited enantiomeric selectivity for the R and S forms of rolipram and generally much higher $IC_{50}$ values (Table 4). Thus the PDE IVC enzyme produced in yeast appears distinct from that produced in mammalian cells (COS, CHO). By contrast, PDE IVA produced in yeast showed similar rolipram inhibition to the enzyme expressed in COS and CHO cells (Tables 1 and 4). These results could be explained in terms of a specific post-translational modification of the PDEIVC enzyme that only occurs in mammalian cells, for example phosphorylation. It follows that such a modification does not occur to PDE IVA or at least if it does, it has no effect on the ability of the enzyme to be inhibited by rolipram.

In either event knowledge of the primary sequence of PDE IVC is necessary to investigate this phenomenon.

TABLE 4

| Inhibitor | Yeast | | CHO | |
|---|---|---|---|---|
| | IC$_{50}$ (nM) | | | |
| | A | C | A | C |
| R-rolipram | 298 | 1648 | 251 | 186 |
| S-rolipram | 619 | 4771 | 1004 | 1428 |
| Rolipram (racemate) | not determined | 1638 | 287 | 43 |

Expression of PDE IVC in insect cells.

The PDE IVC cDNA was expressed in insect cells using the baculovirus system. Sf9 cell lysates were assayed for PDE activity and inhibition by the enantiomers of rolipram. IC$_{50}$ values were obtained for R-rolipram (104 nM) and for S-rolipram (600nM). Thus the potency of R-rolipram on this version of the enzyme is closer to that of the COS enzyme than the yeast produced PDE IVC.

Comparison of PDE IVC expressed in yeast, COS and Sf9 cells.

The kinetics of cAMP hydrolysis for the different preparations of PDE IVC produced in yeast, COS and Sf9 cells were compared (Table 5). All enzyme preparations demonstrated simple Michaelis-Menten kinetics with K$_m$ values in the low uM range (Table 5). V$_{max}$ values of 0.3 and 0.6 $\mu$moles/min/mg were estimated for the partially purified enzymes from yeast and Sf9 cells.

TABLE 5

| Enzyme source | Km ($\mu$M) | V$_{max}$ ($\mu$moles/min/mg) |
|---|---|---|
| Yeast | 2.5 | 0.6 |
| COS | 0.3 | — |
| Sf9 | 1.1 | 0.3 |

These data are consistent with reports in the literature for preparations of purified PDE IV enzymes e.g. Wilson et al (1994) Biochem. J. 304. 407; Conti M et al (1995) Biochemistry 34, 7979.

Figure 5:
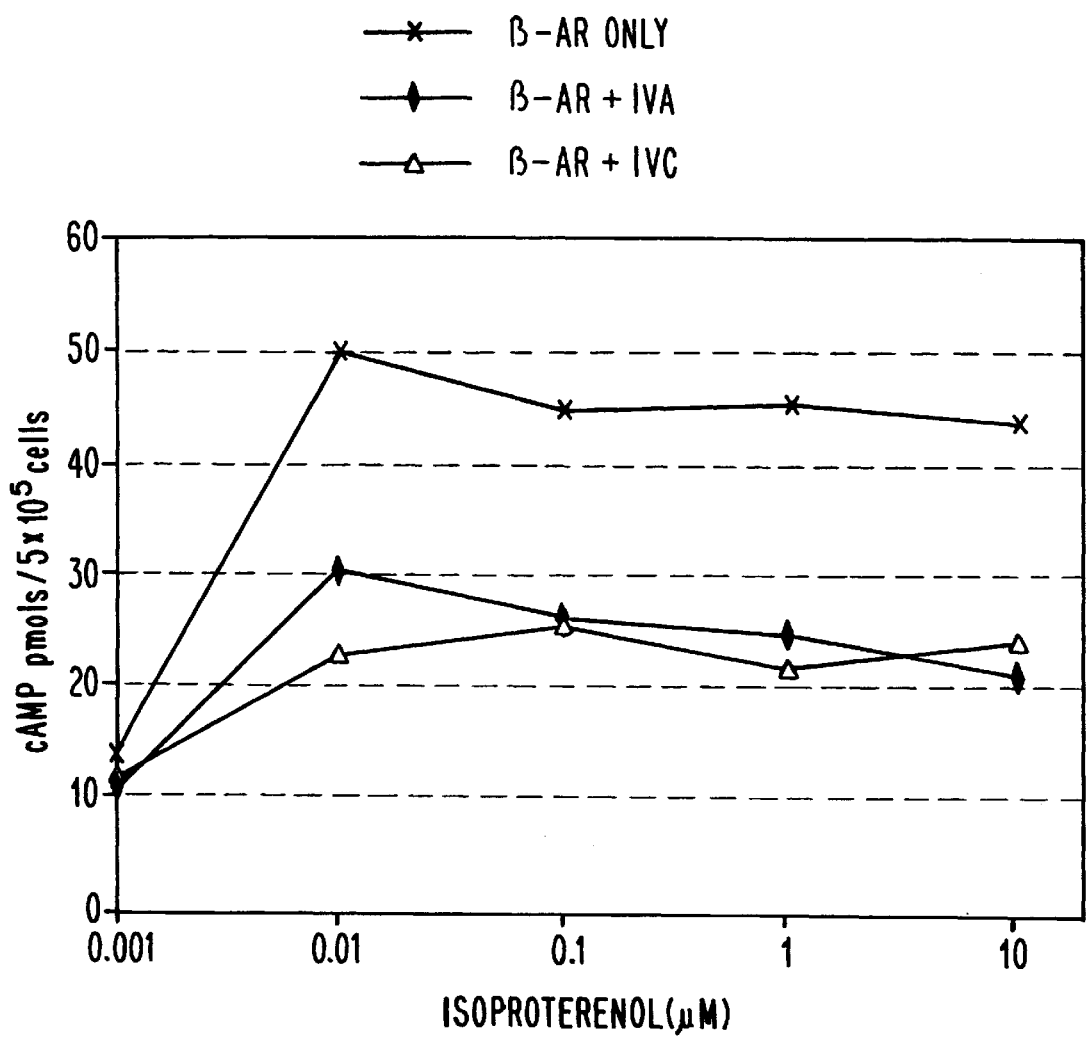
FIG. 5: Elevation of cAMP in CHO cells transfected with beta 2 adrenergic receptor in response to isoptaterenol.

The principal difference between the preparations of the PDE IVC enzyme is in their response to selective PDE IV inhibitors exemplified by rolipram (see Tables 3 and 4). To show that these differences were not due to a contaminant in either one of the preparations, a mixing experiment was carried out. Thus equal amounts of PDE IVC enzyme activity produced in yeast and COS cells were mixed and the inhibition of the mixture by rolipram compared to each component assayed separately. The results (Table 6 and FIG. 5) confirm that the PDE IVC enzymes from yeast and COS cells are distinct. since a 1:1 mixture of the two produces an intermediate value for rolipram inhibition.

TABLE 6

| Enzyme Source | IC$_{50}$ (nM) |
|---|---|
| COS | 75 |
| Yeast | 2051 |
| COS/yeast (1:1 mixture) | 596 |

Deletion of PDE IVC.

Evidence for the biochemical uniqueness of PDE IVC was obtained by comparing the effect of deleting the enzyme to the minimum sequence required for catalysis identified for PDEIV A, B and D. Equivalent deletion mutants of PDE IV C and A were prepared and expressed in COS cells. The results, (Table 7) showed that while both deleted enzymes were expressed only PDEIVA was catalytically active. This indicates that in PDE IVC unlike the other three PDE IV isoforms, catalytic activity requires sequences further towards the amino terminus of the protein

TABLE 7

| Construct (pmol/min/ul) | Expression (Wblot) | Catalytic activity |
|---|---|---|
| PDE IVC Met 1 | + | 0.09 |
| PDE IVC Met 180 | + | 0.0045 |
| PDE IVA Met1 | + | 0.155 |
| PDE IVA Met 330 | + | 0.248 |
| Mock transfection | − | 0.006 |

Inhibition of PDE IV in CHO cells in situ following elevation of CAMP.

A recombinant cell-based assay was developed in order to evaluate the effect of PDE IV inhibitors on the activity of specific PDE IV gene products in situ. Transient expression in CHO cells of a cloned human beta2 adrenergic receptor resulted in a dose-dependent increase in cAMP levels in response to the beta2 agonist, isopreterenol. Co-transfection of either PDE IVC or PDE IVA into the cells prevented this accumulation of cAMP upon stimulation of adenyl cyclase, though the base line level of cAMP was not affected ( FIG. 5 ).

Figure 6:
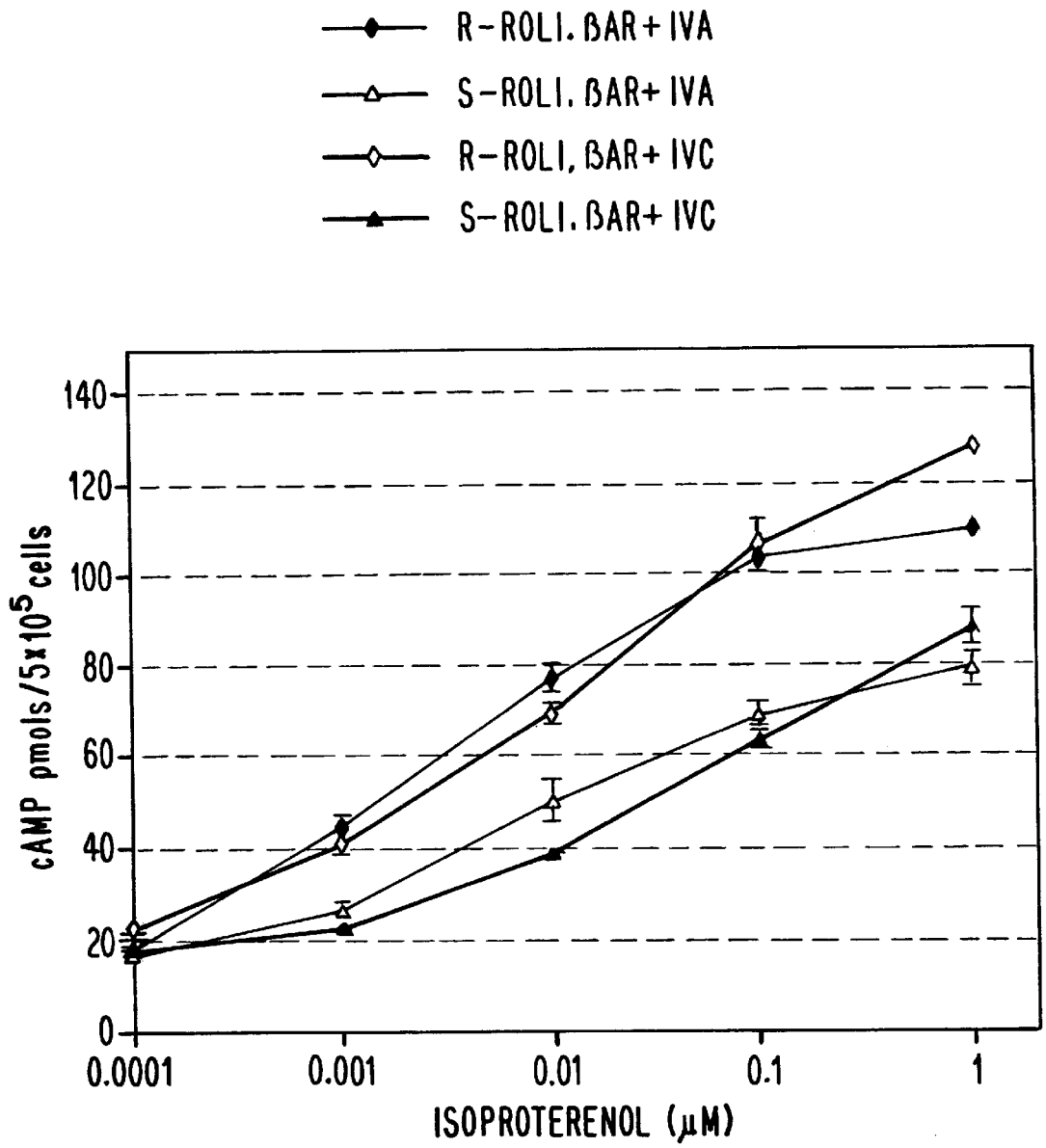
FIG. 6: Effect of R- and S-rolipram on the elevation of cAMP in CHO cells transfected with beta 2 adrenergic receptor+PDE IVC or PDE IVA.
Figure 8:
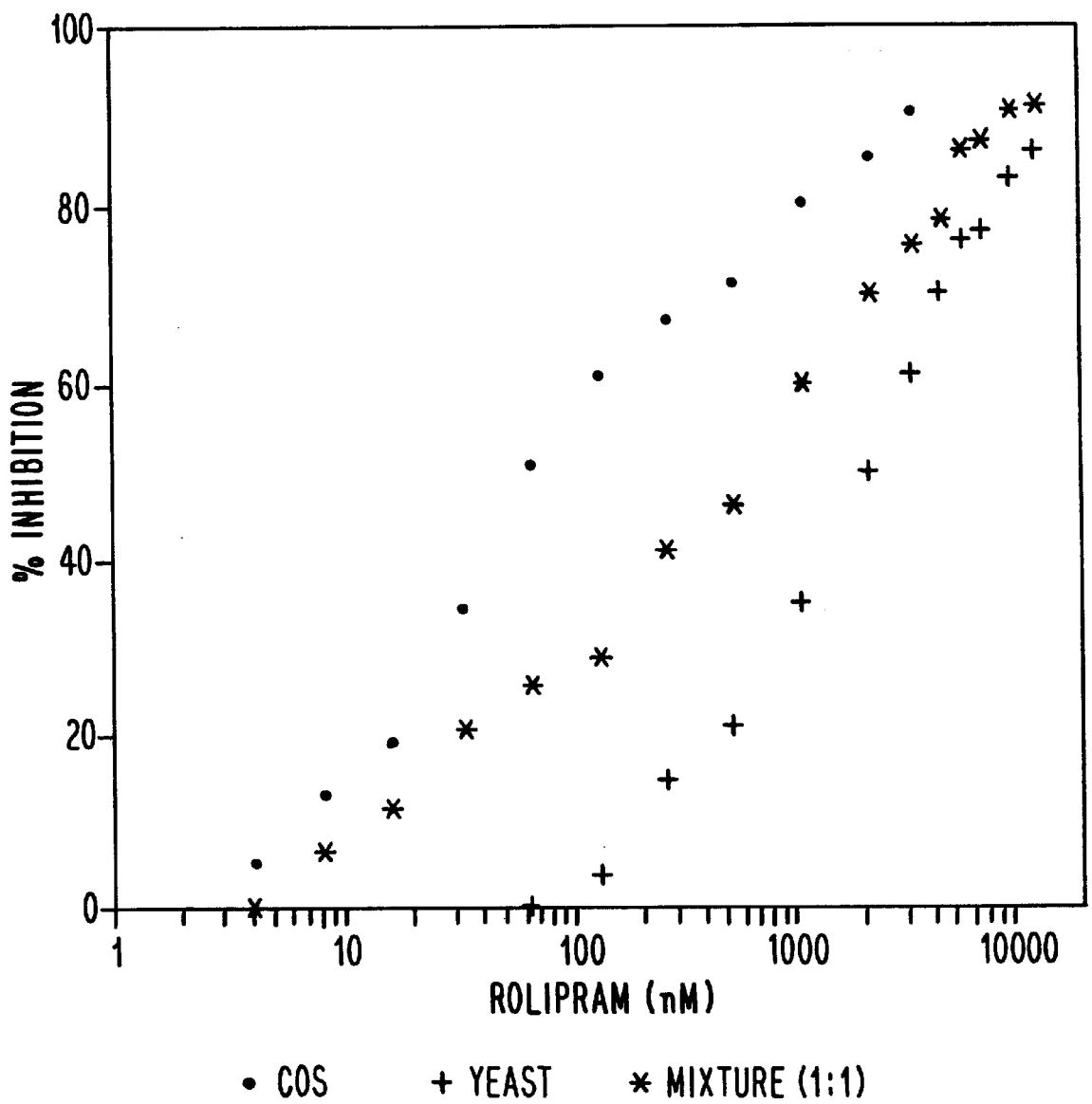
FIG. 8: Inhibition by rolipram of PDE IVC produced in yeast and COS cells and a yeast/COS cell mixture.

This effect was reversed by the addition of rolipram and showed marked enantiomeric selectivity (FIG. 6) This approximately tenfold stereo-selectivity was shown by both A and C and contrasted with the results of in vitro assays on enzymes produced in the same cell type, CHO, in which only PEIVC showed this tenfold selectivity (Table 4).

The significance of this observation is that for a number of biological effects of rolipram both in vitro and in vivo the inhibitor shows marked stereo-selectivity in its potency. For example, R-rolipram is approximately 50 times more effective in the suppression of TNF release from T lymphocytes (Sommer N. et al. 1995 Nature Medicine L244–248). Similarly R-rolipram is 15–30 times more potent than S-rolipram in producing behavioural responses in rodent models of depression ( e.g. Schmiechen R. et al. 1990 Psychopharmacology 102 17–20). This latter effect is closely correlated with the higher affinity of R-rolipram over S-rolipram for binding sites in the rodent forebrain tissue (Schmiechen et al. ibid.; Kaulen P. et al. 1989 Brain Res. 503 229–245.). It has been shown that recombinant PDE IV (Torphy T. et al., 1992 J.Biol.Chem. 267 1798–1804) also show stereoselectivity for high affinity binding to rolipram. This indicates that the binding site(s) for rolipram in vivo correspond to a PDE IV(s).

Recombinant human PDE IV enzymes expressed in a mammalian cell system may be assumed to more closely model the native enzyme than the same enzyme produced in a non-mammalian cell host e.g. yeast and bacteria. It appears that both PDE IV A and PDE IVC and probably B and D, show a similar stereoselectivity for inhibition by the PDE IV specific inhibitor rolipram and presumably other close analogues when evaluated in situ. This correlates with some of the biological effects of rolipram in vivo which may be desirable for the development of novel therapies e.g. anti-inflammatory and anti-depressive. However, most interestingly and unexpected is the observation herein that only the PDE IVC gene product maintains this rolipram stereoselectivity following extraction from transfected cells. Thus this enzyme advantageously allows the evaluation of the properties of PDE IV inhibitors in an in vitro assay.

We claim:

1. A recombinant phosphodiesterase comprising the amino acid sequence of FIGS. 2A to 2C herein (SEQ, ID No: 32), or a catalytically active fragment thereof.

2. A R- and S-rolipram stereoselective conformer of the phosphodiesterase according to claim 2.

3. A conformer according to claim 2 obtainable from mammalian or insect cells.

4. A recombinant phosphodiesterase according to claim 1 in isolated form.

5. A recombinant phosphodiesterase according to claim 2 in isolated form.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 44 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

GATCGGATCC GCGGCTGCCA TCCACGATGT GGATCACCCT GGGG    44

( 2 ) INFORMATION FOR SEQ ID NO:2:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTTTGGATC CGGGATCAGG TAGGGTCTC    29

( 2 ) INFORMATION FOR SEQ ID NO:3:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTTTTAAGCT TCAGCTCATG ACCCAGATAA G    31

( 2 ) INFORMATION FOR SEQ ID NO:4:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

TTTGGATCCG ATAGAATGTT CATCTCCAC    29

( 2 ) INFORMATION FOR SEQ ID NO:5:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTTTTGAATT CGATATCTTC CAGAACCTCA GCGC    34

( 2 ) INFORMATION FOR SEQ ID NO:6:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear (x i) SEQUENCE DESCRIPTION: SEQ ID NO:6:

TTTTGAATT CCTAAGTCCT CTGGTTGTCG AG                                    32

(2) INFORMATION FOR SEQ ID NO:7:

(i) SEQUENCE CHARACTERISTICS:
        (A) LENGTH: 31 bases
        (B) TYPE: nucleic acid
        (C) STRANDEDNESS: single
        (D) TOPOLOGY: linear (x i) SEQUENCE DESCRIPTION: SEQ ID NO:7:

TTTTTGAATT CAGAGTTGTC TGGTAACCGG C                                    31

(2) INFORMATION FOR SEQ ID NO:8:

(i) SEQUENCE CHARACTERISTICS:
        (A) LENGTH: 29 bases
        (B) TYPE: nucleic acid
        (C) STRANDEDNESS: single
        (D) TOPOLOGY: linear (x i) SEQUENCE DESCRIPTION: SEQ ID NO:8:

TTTTGAATTC GTTACGTGTC AGGAGAACG                                       29

(2) INFORMATION FOR SEQ ID NO:9:

(i) SEQUENCE CHARACTERISTICS:
        (A) LENGTH: 45 bases
        (B) TYPE: nucleic acid
        (C) STRANDEDNESS: single
        (D) TOPOLOGY: linear (x i) SEQUENCE DESCRIPTION: SEQ ID NO:9:

CGCGCGAAGC TTATGGAGAC GCTGGAGGAR YTRGACTGGT GTATG                     45

(2) INFORMATION FOR SEQ ID NO:10:

(i) SEQUENCE CHARACTERISTICS:
        (A) LENGTH: 36 bases
        (B) TYPE: nucleic acid
        (C) STRANDEDNESS: single
        (D) TOPOLOGY: linear (x i) SEQUENCE DESCRIPTION: SEQ ID NO:10:

TTTCTCGAGG GTTTCGGACA GGTGGGTCAA CTCCCG                               36

(2) INFORMATION FOR SEQ ID NO:11:

(i) SEQUENCE CHARACTERISTICS:
        (A) LENGTH: 33 bases
        (B) TYPE: nucleic acid
        (C) STRANDEDNESS: single
        (D) TOPOLOGY: linear (x i) SEQUENCE DESCRIPTION: SEQ ID NO:11:

TTTCTCGAGG CCACTGATCC GGGACATGGG CTG                                  33

(2) INFORMATION FOR SEQ ID NO:12:

(i) SEQUENCE CHARACTERISTICS:
        (A) LENGTH: 33 bases
        (B) TYPE: nucleic acid
        (C) STRANDEDNESS: single
        (D) TOPOLOGY: linear (x i) SEQUENCE DESCRIPTION: SEQ ID NO:12:

TTTCTCGAGC CACTTGTTGG TGTCTTCTAG CTC              33

( 2 ) INFORMATION FOR SEQ ID NO:13:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear ( x i ) SEQUENCE DESCRIPTION: SEQ ID NO:13:

TTTGGATCCG GCCAGGACCT GGGCAAAGGG CG               32

( 2 ) INFORMATION FOR SEQ ID NO:14:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( x i ) SEQUENCE DESCRIPTION: SEQ ID NO:14:

TTTGGATCCG GCCTTGGGCG AGAGTTCATA GTCGC            35

( 2 ) INFORMATION FOR SEQ ID NO:15:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:15:

TTTTTAAGCT TGACCTCTGT CCCTGTTCCC CTCC             34

( 2 ) INFORMATION FOR SEQ ID NO:16:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:16:

TTTTGGATC CGGCTGGAAG ACTGAGCCTG GACC              34

( 2 ) INFORMATION FOR SEQ ID NO:17:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:17:

TTTTGGATC CGCATGCCAG CTATGTGGTA GGG               33

( 2 ) INFORMATION FOR SEQ ID NO:18:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( x i ) SEQUENCE DESCRIPTION: SEQ ID NO:18:

TTTTGAATT CGGCAGACAA AGGGACAAGT GAGAAG            36

( 2 ) INFORMATION FOR SEQ ID NO:19:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear ( x i ) SEQUENCE DESCRIPTION: SEQ ID NO:19:

TTTTTAAGCT TCAGCCCTGC GTGAACTGCA GG        32

( 2 ) INFORMATION FOR SEQ ID NO:20:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:20:

TTTTTGAATT CGACTCAAGA GTGACCACTG GAG        33

( 2 ) INFORMATION FOR SEQ ID NO:21:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:21:

TTTTTAAGCT TCCAAAGTGC ATGTCACATG CCAC        34

( 2 ) INFORMATION FOR SEQ ID NO:22:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:22:

TTTTTGAATT CGAGGTCAGT GCAGCTCACT GAAC        34

( 2 ) INFORMATION FOR SEQ ID NO:23:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:23:

TTTTAAGCTT CCACCATGGA ACCCCGACC GTC        33

( 2 ) INFORMATION FOR SEQ ID NO:24:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO:24:

TTTTGCGCTG CGGATCCGGA TGGG        24

( 2 ) INFORMATION FOR SEQ ID NO:25:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:25:

TTTTTGGATC CAGCCCATGT CCCAAATCAC 30

( 2 ) INFORMATION FOR SEQ ID NO:26:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:26:

TTTTTGAATT CCTCGAGCAC CGACTCATCG 30

( 2 ) INFORMATION FOR SEQ ID NO:27:

( i ) SEQUENCE CHARACTERISTICS:
        ( A ) LENGTH: 40 bases
        ( B ) TYPE: nucleic acid
        ( C ) STRANDEDNESS: single
        ( D ) TOPOLOGY: linear ( x i ) SEQUENCE DESCRIPTION: SEQ ID NO:27:

GCGCGCAAGC TTGCCACCAT GTCCCGGATC AGTGGCCTAC 40

( 2 ) INFORMATION FOR SEQ ID NO:28:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( x i ) SEQUENCE DESCRIPTION: SEQ ID NO:28:

GAACACAGCC TCGAGGGCGG GCGTAGCC 28

( 2 ) INFORMATION FOR SEQ ID NO:29:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:29:

GCGCGCAAGC TTCGCTTACC TGCCAGACTG CGC 33

( 2 ) INFORMATION FOR SEQ ID NO:30:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:30:

GCGCGCGAAT TCTCTGTTTA GTGTTCTGTT GGG 33

( 2 ) INFORMATION FOR SEQ ID NO:31:

( i ) SEQUENCE CHARACTERISTICS:
    ( A ) LENGTH: 2153 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:31:

```
TTCGACGTGA TCAGACCCAA CTCAGACCCG GTCATACTTG GACCGAATGC TGCCAAATCC         60

CCCACCTCTA CCCAGATCTG AGCCTACGCG GGGTGCCGAC CCAGCTCGTG GACGGGGATA        120

CGGTGACCTT TGACCCAAAA GTCTTGGCCG GGACCAGCCG GACACTGGCC CTCGGCCGGG        180

AGCTCCGAGT CTCAGGCGGT CCCGGTTGTC TTCCTGTCGG TGCCGCTTCC GCCTGCCCTT        240

CTTGAAAACC CACCCCCAGC TTTGACCTGG AAAATGGGCT CTCGTGTGGG AGGAGGGCCC        300

TGGACCCTCA GTCCAGCCCT GGCCTGGGCC GGATT ATG CAG GCT CCA GTC CCG          353
                                       Met Gln Ala Pro Val Pro
                                         1                   5

CAC AGC CAG CGG CGC GAG TCC TTC CTG TAC CGC TCA GAT AGC GAC TAT         401
His Ser Gln Arg Arg Glu Ser Phe Leu Tyr Arg Ser Asp Ser Asp Tyr
             10                  15                  20

GAA CTC TCG CCC AAG GCC ATG TCT CGG AAC TCC TCT GTG GCC AGC GAC         449
Glu Leu Ser Pro Lys Ala Met Ser Arg Asn Ser Ser Val Ala Ser Asp
         25                  30                  35

CTA CAT GGA GAG GAC ATG ATT GTG ACG CCC TTT GCC CAG GTC CTG GCC         497
Leu His Gly Glu Asp Met Ile Val Thr Pro Phe Ala Gln Val Leu Ala
 40                  45                  50

AGT CTG CGG ACC GTT CGG AGC AAC GTG GCG GCC CTT GCC CGC CAG CAA         545
Ser Leu Arg Thr Val Arg Ser Asn Val Ala Ala Leu Ala Arg Gln Gln
 55                  60                  65                  70

TGC CTA GGA GCA GCC AAG CAG GGA CCC GTC GGA AAC CCT TCA TCC AGC         593
Cys Leu Gly Ala Ala Lys Gln Gly Pro Val Gly Asn Pro Ser Ser Ser
                 75                  80                  85

AAT CAG CTC CCT CCT GCA GAG GAC ACG GGG CAG AAG CTG GCA TTG GAG         641
Asn Gln Leu Pro Pro Ala Glu Asp Thr Gly Gln Lys Leu Ala Leu Glu
         90                  95                 100

ACG CTA GAC GAG CTG GAC TGG TGC CTG GAT CAG TTG GAG ACG CTG CAG         689
Thr Leu Asp Glu Leu Asp Trp Cys Leu Asp Gln Leu Glu Thr Leu Gln
    105                 110                 115

ACC CGG CAC TCG GTG GGG GAG ATG GCC TCC AAC AAG TTC AAG CGG ATC         737
Thr Arg His Ser Val Gly Glu Met Ala Ser Asn Lys Phe Lys Arg Ile
120                 125                 130

CTG AAC CGG GAG TTG ACC CAC CTG TCC GAA ACC AGC CGC TCC GGG AAC         785
Leu Asn Arg Glu Leu Thr His Leu Ser Glu Thr Ser Arg Ser Gly Asn
135                 140                 145                 150

CAG GTG TCC GAG TAC ATC TCC CGG ACC TTC CTG GAC CAG CAG ACC GAG         833
Gln Val Ser Glu Tyr Ile Ser Arg Thr Phe Leu Asp Gln Gln Thr Glu
                155                 160                 165

GTG GAG CTG CCC AAG GTG ACC GCT GAG GAG GCC CCA CAG CCC ATG TCC         881
Val Glu Leu Pro Lys Val Thr Ala Glu Glu Ala Pro Gln Pro Met Ser
            170                 175                 180

CGG ATC AGT GGC CTA CAT GGG CTC TGC CAC AGT GCC AGC CTC TCC TCA         929
Arg Ile Ser Gly Leu His Gly Leu Cys His Ser Ala Ser Leu Ser Ser
        185                 190                 195

GCC ACT GTC CCA CGC TTT GGG GTC CAG ACT GAC CAG GAG GAG CAA CTG         977
Ala Thr Val Pro Arg Phe Gly Val Gln Thr Asp Gln Glu Glu Gln Leu
    200                 205                 210

GCC AAG GAG CTA GAA GAC ACC AAC AAG TGG GGA CTT GAT GTG TTC AAG        1025
Ala Lys Glu Leu Glu Asp Thr Asn Lys Trp Gly Leu Asp Val Phe Lys
215                 220                 225                 230

GTG GCG GAG CTA AGT GGG AAC CAG CCC CTC ACA GCT ATC ATA TTC AGC        1073
Val Ala Glu Leu Ser Gly Asn Gln Pro Leu Thr Ala Ile Ile Phe Ser
```

-continued

|  |  |  | 235 |  |  |  |  | 240 |  |  |  |  | 245 |  |  |  |
|---|---|---|---|---|---|---|---|---|---|---|---|---|---|---|---|---|
| ATT | TTT | CAG | GAG | CGG | GAC | CTG | CTG | AAG | ACA | TTC | CAG | ATC | CCA | GCA | GAC | 1121 |
| Ile | Phe | Gln | Glu 250 | Arg | Asp | Leu | Leu | Lys 255 | Thr | Phe | Gln | Ile | Pro 260 | Ala | Asp | |
| ACA | CTG | GCC | ACC | TAC | CTG | CTG | ATG | CTG | GAG | GGT | CAC | TAC | CAC | GCC | AAT | 1169 |
| Thr | Leu | Ala 265 | Thr | Tyr | Leu | Leu | Met 270 | Leu | Glu | Gly | His | Tyr 275 | His | Ala | Asn | |
| GTG | GCC | TAC | CAC | AAC | AGC | CTA | CAT | GCC | GCC | GAC | GTG | GCC | CAG | TCC | ACG | 1217 |
| Val | Ala 280 | Tyr | His | Asn | Ser | Leu 285 | His | Ala | Ala | Asp | Val 290 | Ala | Gln | Ser | Thr | |
| CAT | GTG | CTG | CTG | GCT | ACG | CCC | GCC | CTC | GAG | GCT | GTG | TTC | ACA | GAC | TTG | 1265 |
| His 295 | Val | Leu | Leu | Ala | Thr 300 | Pro | Ala | Leu | Glu | Ala 305 | Val | Phe | Thr | Asp | Leu 310 | |
| GAA | ATC | CTG | GCT | GCC | CTC | TTT | GCA | AGC | GCC | ATC | CAC | GAC | GTG | GAC | CAT | 1313 |
| Glu | Ile | Leu | Ala | Ala 315 | Leu | Phe | Ala | Ser | Ala 320 | Ile | His | Asp | Val | Asp 325 | His | |
| CCT | GGG | GTC | TCC | AAC | CAG | TTT | CTG | ATT | AAC | ACC | AAC | TCA | GAG | CTG | GCG | 1361 |
| Pro | Gly | Val | Ser 330 | Asn | Gln | Phe | Leu | Ile 335 | Asn | Thr | Asn | Ser | Glu 340 | Leu | Ala | |
| CTT | ATG | TAC | AAC | GAC | GCC | TCG | GTG | CTG | GAG | AAC | CAT | CAC | CTG | GCT | GTG | 1409 |
| Leu | Met | Tyr 345 | Asn | Asp | Ala | Ser | Val 350 | Leu | Glu | Asn | His | His 355 | Leu | Ala | Val | |
| GGC | TTC | AAG | CTG | CTG | CAG | GCA | GAG | AAC | TGC | GAT | ATC | TTC | CAG | AAC | CTC | 1457 |
| Gly | Phe | Lys 360 | Leu | Leu | Gln | Ala | Glu 365 | Asn | Cys | Asp | Ile | Phe 370 | Gln | Asn | Leu | |
| AGC | GCC | AAG | CAG | CGA | CTG | AGT | CTG | CGC | AGG | ATG | GTC | ATT | GAC | ATG | GTG | 1505 |
| Ser | Ala | Lys 375 | Gln | Arg | Leu | Ser 380 | Leu | Arg | Arg | Met | Val 385 | Ile | Asp | Met | Val 390 | |
| CTG | GCC | ACA | GAC | ATG | TCC | AAA | CAC | ATG | AAC | CTC | CTG | GCC | GAC | CTC | AAG | 1553 |
| Leu | Ala | Thr | Asp | Met 395 | Ser | Lys | His | Met | Asn 400 | Leu | Leu | Ala | Asp | Leu 405 | Lys | |
| ACC | ATG | GTG | GAG | ACC | AAG | AAG | GTG | ACA | AGC | CTC | GGT | GTC | CTC | CTC | CTG | 1601 |
| Thr | Met | Val | Glu 410 | Thr | Lys | Lys | Val | Thr 415 | Ser | Leu | Gly | Val | Leu 420 | Leu | Leu | |
| GAC | AAC | TAT | TCC | GAC | CGA | ATC | CAG | GTC | TTG | CAG | AAC | CTG | GTG | CAC | TGT | 1649 |
| Asp | Asn | Tyr 425 | Ser | Asp | Arg | Ile | Gln 430 | Val | Leu | Gln | Asn | Leu 435 | Val | His | Cys | |
| GCT | GAT | CTG | AGC | AAC | CCC | ACC | AAG | CCG | CTG | CCC | CTG | TAC | CGC | CAG | TGG | 1697 |
| Ala | Asp 440 | Leu | Ser | Asn | Pro | Thr 445 | Lys | Pro | Leu | Pro | Leu 450 | Tyr | Arg | Gln | Trp | |
| ACG | GAC | CGC | ATC | ATG | GCC | GAG | TTC | TTC | CAG | CAG | GGA | GAC | CGC | GAG | CGT | 1745 |
| Thr | Asp | Arg 455 | Ile | Met | Ala | Glu 460 | Phe | Phe | Gln | Gln | Gly 465 | Asp | Arg | Glu | Arg 470 | |
| GAG | TCG | GGC | CTG | GAC | ATC | AGT | CCC | ATG | TGT | GAC | AAG | CAT | ACG | GCC | TCA | 1793 |
| Glu | Ser | Gly | Leu | Asp 475 | Ile | Ser | Pro | Met | Cys 480 | Asp | Lys | His | Thr | Ala 485 | Ser | |
| GTG | GAG | AAG | TCC | CAG | GTG | GGT | TTC | ATT | GAC | TAC | ATT | GCT | CAC | CCA | CTG | 1841 |
| Val | Glu | Lys | Ser 490 | Gln | Val | Gly | Phe | Ile 495 | Asp | Tyr | Ile | Ala | His 500 | Pro | Leu | |
| TGG | GAG | ACT | TGG | GCT | GAC | CTG | GTC | CAC | CCA | GAT | GCA | CAG | GAC | CTG | CTG | 1889 |
| Trp | Glu | Thr | Trp 505 | Ala | Asp | Leu | Val | His 510 | Pro | Asp | Ala | Gln | Asp 515 | Leu | Leu | |
| GAC | ACG | CTG | GAG | GAC | AAT | CGA | GAG | TGG | TAC | CAG | AGC | AAG | ATC | CCC | CGA | 1937 |
| Asp | Thr | Leu 520 | Glu | Asp | Asn | Arg | Glu 525 | Trp | Tyr | Gln | Ser | Lys 530 | Ile | Pro | Arg | |
| AGT | CCC | TCA | GAC | CTC | ACC | AAC | CCC | GAG | CGG | GAC | GGG | CCT | GAC | AGA | TTC | 1985 |
| Ser | Pro 535 | Ser | Asp | Leu | Thr | Asn 540 | Pro | Glu | Arg | Asp | Gly 545 | Pro | Asp | Arg | Phe 550 | |
| CAG | TTT | GAA | CTG | ACT | CTG | GAG | GAG | GCA | GAG | GAA | GAG | GAT | GAG | GAG | GAA | 2033 |
| Gln | Phe | Glu | Leu | Thr | Leu | Glu | Glu | Ala | Glu | Glu | Glu | Asp | Glu | Glu | Glu | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 555 |     |     |     |     | 560 |     |     |     |     | 565 |     |      |
| GAA | GAG | GAG | GGG | GAA | GAG | ACA | GCT | TTA | GCC | AAA | GAG | GCC | TTG | GAG | TTG | 2081 |
| Glu | Glu | Glu | Gly | Glu | Glu | Thr | Ala | Leu | Ala | Lys | Glu | Ala | Leu | Glu | Leu |      |
|     |     |     | 570 |     |     |     |     | 575 |     |     |     |     | 580 |     |     |      |
| CCT | GAC | ACT | GAA | CTC | CTG | TCC | CCT | GAA | GCC | GGC | CCA | GCC | CCT | GGG | GAC | 2129 |
| Pro | Asp | Thr | Glu | Leu | Leu | Ser | Pro | Glu | Ala | Gly | Pro | Ala | Pro | Gly | Asp |      |
|     |     | 585 |     |     |     |     | 590 |     |     |     |     | 595 |     |     |     |      |
| TTA | CCC | CTC | GAC | AAC | CAG | AGG | ACT |     |     |     |     |     |     |     |     | 2153 |
| Leu | Pro | Leu | Asp | Asn | Gln | Arg | Thr |     |     |     |     |     |     |     |     |      |
| 600 |     |     |     |     | 605 |     |     |     |     |     |     |     |     |     |     |      |

( 2 ) INFORMATION FOR SEQ ID NO:32:

( i ) SEQUENCE CHARACTERISTICS:
        ( A ) LENGTH: 606 amino acids
        ( B ) TYPE: amino acid
        ( D ) TOPOLOGY: unknown ( x i ) SEQUENCE DESCRIPTION: SEQ ID NO:32:

| Met | Gln | Ala | Pro | Val | Pro | His | Ser | Gln | Arg | Arg | Glu | Ser | Phe | Leu | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Ser | Asp | Ser | Asp | Tyr | Glu | Leu | Ser | Pro | Lys | Ala | Met | Ser | Arg | Asn |
|     |     |     | 20  |     |     |     |     | 25  |     |     |     |     | 30  |     |     |
| Ser | Ser | Val | Ala | Ser | Asp | Leu | His | Gly | Glu | Asp | Met | Ile | Val | Thr | Pro |
|     |     | 35  |     |     |     |     | 40  |     |     |     |     | 45  |     |     |     |
| Phe | Ala | Gln | Val | Leu | Ala | Ser | Leu | Arg | Thr | Val | Arg | Ser | Asn | Val | Ala |
|     | 50  |     |     |     |     | 55  |     |     |     |     | 60  |     |     |     |     |
| Ala | Leu | Ala | Arg | Gln | Gln | Cys | Leu | Gly | Ala | Ala | Lys | Gln | Gly | Pro | Val |
| 65  |     |     |     |     | 70  |     |     |     |     | 75  |     |     |     |     | 80  |
| Gly | Asn | Pro | Ser | Ser | Ser | Asn | Gln | Leu | Pro | Pro | Ala | Glu | Asp | Thr | Gly |
|     |     |     |     | 85  |     |     |     |     | 90  |     |     |     |     | 95  |     |
| Gln | Lys | Leu | Ala | Leu | Glu | Thr | Leu | Asp | Glu | Leu | Asp | Trp | Cys | Leu | Asp |
|     |     |     |     | 100 |     |     |     |     | 105 |     |     |     |     | 110 |     |
| Gln | Leu | Glu | Thr | Leu | Gln | Thr | Arg | His | Ser | Val | Gly | Glu | Met | Ala | Ser |
|     |     |     |     | 115 |     |     |     |     | 120 |     |     |     |     | 125 |     |
| Asn | Lys | Phe | Lys | Arg | Ile | Leu | Asn | Arg | Glu | Leu | Thr | His | Leu | Ser | Glu |
|     | 130 |     |     |     |     | 135 |     |     |     |     | 140 |     |     |     |     |
| Thr | Ser | Arg | Ser | Gly | Asn | Gln | Val | Ser | Glu | Tyr | Ile | Ser | Arg | Thr | Phe |
| 145 |     |     |     |     | 150 |     |     |     |     | 155 |     |     |     |     | 160 |
| Leu | Asp | Gln | Gln | Thr | Glu | Val | Glu | Leu | Pro | Lys | Val | Thr | Ala | Glu | Glu |
|     |     |     |     | 165 |     |     |     |     | 170 |     |     |     |     | 175 |     |
| Ala | Pro | Gln | Pro | Met | Ser | Arg | Ile | Ser | Gly | Leu | His | Gly | Leu | Cys | His |
|     |     |     | 180 |     |     |     |     | 185 |     |     |     |     | 190 |     |     |
| Ser | Ala | Ser | Leu | Ser | Ser | Ala | Thr | Val | Pro | Arg | Phe | Gly | Val | Gln | Thr |
|     |     | 195 |     |     |     |     | 200 |     |     |     |     | 205 |     |     |     |
| Asp | Gln | Glu | Glu | Gln | Leu | Ala | Lys | Glu | Leu | Glu | Asp | Thr | Asn | Lys | Trp |
|     | 210 |     |     |     |     | 215 |     |     |     |     | 220 |     |     |     |     |
| Gly | Leu | Asp | Val | Phe | Lys | Val | Ala | Glu | Leu | Ser | Gly | Asn | Gln | Pro | Leu |
| 225 |     |     |     |     | 230 |     |     |     |     | 235 |     |     |     |     | 240 |
| Thr | Ala | Ile | Ile | Phe | Ser | Ile | Phe | Gln | Glu | Arg | Asp | Leu | Leu | Lys | Thr |
|     |     |     |     | 245 |     |     |     |     | 250 |     |     |     |     | 255 |     |
| Phe | Gln | Ile | Pro | Ala | Asp | Thr | Leu | Ala | Thr | Tyr | Leu | Leu | Met | Leu | Glu |
|     |     |     | 260 |     |     |     |     | 265 |     |     |     |     | 270 |     |     |
| Gly | His | Tyr | His | Ala | Asn | Val | Ala | Tyr | His | Asn | Ser | Leu | His | Ala | Ala |
|     |     | 275 |     |     |     |     | 280 |     |     |     |     | 285 |     |     |     |
| Asp | Val | Ala | Gln | Ser | Thr | His | Val | Leu | Leu | Ala | Thr | Pro | Ala | Leu | Glu |
|     | 290 |     |     |     |     | 295 |     |     |     |     | 300 |     |     |     |     |

```
Ala  Val  Phe  Thr  Asp  Leu  Glu  Ile  Leu  Ala  Ala  Leu  Phe  Ala  Ser  Ala
305                      310                 315                     320

Ile  His  Asp  Val  Asp  His  Pro  Gly  Val  Ser  Asn  Gln  Phe  Leu  Ile  Asn
                    325                 330                          335

Thr  Asn  Ser  Glu  Leu  Ala  Leu  Met  Tyr  Asn  Asp  Ala  Ser  Val  Leu  Glu
               340                      345                     350

Asn  His  His  Leu  Ala  Val  Gly  Phe  Lys  Leu  Leu  Gln  Ala  Glu  Asn  Cys
          355                      360                     365

Asp  Ile  Phe  Gln  Asn  Leu  Ser  Ala  Lys  Gln  Arg  Leu  Ser  Leu  Arg  Arg
     370                      375                     380

Met  Val  Ile  Asp  Met  Val  Leu  Ala  Thr  Asp  Met  Ser  Lys  His  Met  Asn
385                      390                     395                          400

Leu  Leu  Ala  Asp  Leu  Lys  Thr  Met  Val  Glu  Thr  Lys  Lys  Val  Thr  Ser
                    405                      410                     415

Leu  Gly  Val  Leu  Leu  Leu  Asp  Asn  Tyr  Ser  Asp  Arg  Ile  Gln  Val  Leu
                    420                      425                     430

Gln  Asn  Leu  Val  His  Cys  Ala  Asp  Leu  Ser  Asn  Pro  Thr  Lys  Pro  Leu
          435                      440                     445

Pro  Leu  Tyr  Arg  Gln  Trp  Thr  Asp  Arg  Ile  Met  Ala  Glu  Phe  Phe  Gln
     450                      455                     460

Gln  Gly  Asp  Arg  Glu  Arg  Glu  Ser  Gly  Leu  Asp  Ile  Ser  Pro  Met  Cys
465                      470                     475                          480

Asp  Lys  His  Thr  Ala  Ser  Val  Glu  Lys  Ser  Gln  Val  Gly  Phe  Ile  Asp
                    485                      490                     495

Tyr  Ile  Ala  His  Pro  Leu  Trp  Glu  Thr  Trp  Ala  Asp  Leu  Val  His  Pro
               500                      505                     510

Asp  Ala  Gln  Asp  Leu  Leu  Asp  Thr  Leu  Glu  Asp  Asn  Arg  Glu  Trp  Tyr
          515                      520                     525

Gln  Ser  Lys  Ile  Pro  Arg  Ser  Pro  Ser  Asp  Leu  Thr  Asn  Pro  Glu  Arg
     530                      535                     540

Asp  Gly  Pro  Asp  Arg  Phe  Gln  Phe  Glu  Leu  Thr  Leu  Glu  Glu  Ala  Glu
545                      550                     555                          560

Glu  Glu  Asp  Glu  Glu  Glu  Glu  Glu  Glu  Gly  Glu  Glu  Thr  Ala  Leu  Ala
                    565                      570                     575

Lys  Glu  Ala  Leu  Glu  Leu  Pro  Asp  Thr  Glu  Leu  Leu  Ser  Pro  Glu  Ala
               580                      585                     590

Gly  Pro  Ala  Pro  Gly  Asp  Leu  Pro  Leu  Asp  Asn  Gln  Arg  Thr
          595                      600                     605
```

( 2 ) INFORMATION FOR SEQ ID NO:33:

( i ) SEQUENCE CHARACTERISTICS:
        ( A ) LENGTH: 885 amino acids
        ( B ) TYPE: amino acid
        ( D ) TOPOLOGY: unknown ( x i ) SEQUENCE DESCRIPTION: SEQ ID NO:33:

```
Met  Glu  Pro  Pro  Thr  Val  Pro  Ser  Glu  Arg  Ser  Leu  Ser  Leu  Ser  Leu
1                   5                   10                      15

Pro  Gly  Pro  Arg  Glu  Gly  Gln  Ala  Thr  Leu  Lys  Pro  Pro  Pro  Gln  His
               20                      25                      30

Leu  Trp  Arg  Gln  Pro  Arg  Thr  Pro  Ile  Arg  Ile  Gln  Gln  Arg  Gly  Tyr
          35                      40                      45

Ser  Asp  Ser  Ala  Glu  Arg  Ala  Glu  Arg  Glu  Arg  Gln  Pro  His  Arg  Pro
     50                      55                      60
```

-continued

| | | | | | | | | | | | | | | |
|---|---|---|---|---|---|---|---|---|---|---|---|---|---|---|
| Ile | Glu | Arg | Ala | Asp | Ala | Met | Asp | Thr | Ser | Asp | Arg | Pro | Gly | Leu | Arg |
| 65 | | | | | 70 | | | | 75 | | | | | | 80 |
| Thr | Thr | Arg | Met | Ser | Trp | Pro | Ser | Ser | Phe | His | Gly | Thr | Gly | Thr | Gly |
| | | | | 85 | | | | | 90 | | | | | 95 | |
| Ser | Gly | Gly | Ala | Gly | Gly | Ser | Ser | Arg | Arg | Phe | Glu | Ala | Glu | Asn | |
| | | | | 100 | | | | | 105 | | | | | 110 | |
| Gly | Thr | Ser | Ala | Gly | Arg | Ser | Pro | Leu | Asp | Pro | Met | Thr | Ser | Pro | Ser |
| | | | | 115 | | | | | 120 | | | | | 125 | |
| Pro | Gly | Leu | Val | Leu | His | Ala | Gly | Ala | Ala | Thr | Ser | Gln | Arg | Arg | Glu |
| | | | 130 | | | | | 135 | | | | | 140 | | |
| Ser | Phe | Leu | Tyr | Arg | Ser | Asp | Ser | Asp | Tyr | Asp | Met | Ser | Pro | Lys | Thr |
| 145 | | | | | 150 | | | | | 155 | | | | | 160 |
| Met | Ser | Arg | Asn | Ser | Ser | Val | Thr | Ser | Glu | Ala | His | Ala | Glu | Asp | Leu |
| | | | | 165 | | | | | 170 | | | | | 175 | |
| Ile | Val | Thr | Pro | Phe | Ala | Gln | Val | Leu | Ala | Ser | Leu | Arg | Ser | Val | Arg |
| | | | 180 | | | | | 185 | | | | | 190 | | |
| Ser | Asn | Phe | Ser | Leu | Leu | Thr | Asn | Val | Pro | Val | Pro | Ser | Asn | Lys | Arg |
| | | | 195 | | | | | 200 | | | | | 205 | | |
| Ser | Pro | Leu | Gly | Gly | Pro | Thr | Pro | Val | Cys | Lys | Ala | Thr | Leu | Ser | Glu |
| | | 210 | | | | | 215 | | | | | 220 | | | |
| Glu | Thr | Cys | Gln | Gln | Leu | Ala | Arg | Glu | Thr | Leu | Glu | Glu | Leu | Asp | Trp |
| 225 | | | | | 230 | | | | | 235 | | | | | 240 |
| Cys | Leu | Glu | Gln | Leu | Glu | Thr | Met | Gln | Thr | Tyr | Arg | Ser | Val | Ser | Glu |
| | | | | 245 | | | | | 250 | | | | | 255 | |
| Met | Ala | Ser | His | Lys | Phe | Lys | Arg | Met | Leu | Asn | Arg | Glu | Leu | Thr | His |
| | | | 260 | | | | | 265 | | | | | 270 | | |
| Leu | Ser | Glu | Met | Ser | Arg | Ser | Gly | Asn | Gln | Val | Ser | Glu | Tyr | Ile | Ser |
| | | 275 | | | | | 280 | | | | | 285 | | | |
| Thr | Thr | Phe | Leu | Asp | Lys | Gln | Asn | Glu | Val | Glu | Ile | Pro | Ser | Pro | Thr |
| | | 290 | | | | | 295 | | | | | 300 | | | |
| Met | Lys | Glu | Arg | Glu | Lys | Gln | Gln | Ala | Pro | Arg | Pro | Arg | Pro | Ser | Pro |
| 305 | | | | | 310 | | | | | 315 | | | | | 320 |
| Pro | Pro | Pro | Pro | Val | Pro | His | Leu | Gln | Pro | Met | Ser | Gln | Ile | Thr | Gly |
| | | | | 325 | | | | | 330 | | | | | 335 | |
| Leu | Lys | Lys | Leu | Met | His | Ser | Asn | Ser | Leu | Asn | Asn | Ser | Asn | Ile | Pro |
| | | | 340 | | | | | 345 | | | | | 350 | | |
| Arg | Phe | Gly | Val | Lys | Thr | Asp | Gln | Glu | Glu | Leu | Leu | Ala | Gln | Glu | Leu |
| | | | 355 | | | | | 360 | | | | | 365 | | |
| Glu | Asn | Leu | Asn | Lys | Trp | Gly | Leu | Asn | Ile | Phe | Cys | Val | Ser | Asp | Tyr |
| | 370 | | | | | 375 | | | | | 380 | | | | |
| Ala | Gly | Gly | Arg | Ser | Leu | Thr | Cys | Ile | Met | Tyr | Met | Ile | Phe | Gln | Glu |
| 385 | | | | | 390 | | | | | 395 | | | | | 400 |
| Arg | Asp | Leu | Leu | Lys | Lys | Phe | Arg | Ile | Pro | Val | Asp | Thr | Met | Val | Thr |
| | | | | 405 | | | | | 410 | | | | | 415 | |
| Tyr | Met | Leu | Thr | Leu | Glu | Asp | His | Tyr | His | Ala | Asp | Val | Ala | Tyr | His |
| | | | 420 | | | | | 425 | | | | | 430 | | |
| Asn | Ser | Leu | His | Ala | Ala | Asp | Val | Leu | Gln | Ser | Thr | His | Val | Leu | Leu |
| | | | 435 | | | | | 440 | | | | | 445 | | |
| Ala | Thr | Pro | Ala | Leu | Asp | Ala | Val | Phe | Thr | Asp | Leu | Glu | Ile | Leu | Ala |
| | | | 450 | | | | | 455 | | | | | 460 | | |
| Ala | Leu | Phe | Ala | Ala | Ala | Ile | His | Asp | Val | Asp | His | Pro | Gly | Val | Ser |
| 465 | | | | | 470 | | | | | 475 | | | | | 480 |
| Asn | Gln | Phe | Leu | Ile | Asn | Thr | Asn | Ser | Glu | Leu | Ala | Leu | Met | Tyr | Asn |
| | | | | 485 | | | | | 490 | | | | | 495 | |

```
Asp  Glu  Ser  Val  Leu  Glu  Asn  His  His  Leu  Ala  Val  Gly  Phe  Lys  Leu
               500                      505                      510

Leu  Gln  Glu  Glu  Asn  Cys  Asp  Ile  Phe  Gln  Asn  Leu  Ser  Lys  Arg  Gln
          515                      520                     525

Arg  Gln  Ser  Leu  Arg  Lys  Met  Val  Ile  Asp  Met  Val  Leu  Ala  Thr  Asp
     530                     535                     540

Met  Ser  Lys  His  Met  Thr  Leu  Leu  Ala  Asp  Leu  Lys  Thr  Met  Val  Glu
545                      550                     555                          560

Thr  Lys  Lys  Val  Thr  Ser  Ser  Gly  Val  Leu  Leu  Asp  Asn  Tyr  Ser
                    565                     570                     575

Asp  Arg  Ile  Gln  Val  Leu  Arg  Asn  Met  Val  His  Cys  Ala  Asp  Leu  Ser
               580                      585                     590

Asn  Pro  Thr  Lys  Pro  Leu  Glu  Leu  Tyr  Arg  Gln  Trp  Thr  Asp  Arg  Ile
          595                      600                     605

Met  Ala  Glu  Phe  Phe  Gln  Gln  Gly  Asp  Arg  Glu  Arg  Glu  Arg  Gly  Met
          610                     615                     620

Glu  Ile  Ser  Pro  Met  Cys  Asp  Lys  His  Thr  Ala  Ser  Val  Glu  Lys  Ser
625                      630                     635                          640

Gln  Val  Gly  Phe  Ile  Asp  Tyr  Ile  Val  His  Pro  Leu  Trp  Glu  Thr  Trp
               645                     650                     655

Ala  Asp  Leu  Val  His  Pro  Asp  Ala  Gln  Ile  Leu  Asp  Thr  Leu  Glu
               660                     665                     670

Asp  Asn  Arg  Asp  Trp  Tyr  Tyr  Ser  Ala  Ile  Arg  Gln  Ser  Pro  Ser  Pro
          675                     680                     685

Pro  Pro  Glu  Glu  Glu  Ser  Arg  Gly  Pro  Gly  His  Pro  Pro  Leu  Pro  Asp
          690                     695                     700

Lys  Phe  Gln  Phe  Glu  Leu  Thr  Leu  Glu  Glu  Glu  Glu  Glu  Glu  Glu  Ile
705                     710                     715                          720

Ser  Arg  Ala  Gln  Ile  Arg  Cys  Thr  Ala  Gln  Glu  Ala  Leu  Thr  Glu  Gln
               725                     730                     735

Gly  Leu  Ser  Gly  Val  Glu  Glu  Ala  Leu  Asp  Ala  Thr  Ile  Ala  Trp  Glu
               740                     745                     750

Ala  Ser  Pro  Ala  Gln  Glu  Ser  Leu  Glu  Val  Met  Ala  Gln  Glu  Ala  Ser
          755                     760                     765

Leu  Glu  Ala  Glu  Leu  Glu  Ala  Val  Tyr  Leu  Thr  Gln  Ala  Gln  Ser
     770                     775                     780

Thr  Gly  Ser  Glu  Pro  Val  Ala  Pro  Asp  Glu  Phe  Ser  Asn  Arg  Glu  Glu
785                     790                     795                          800

Phe  Val  Val  Ala  Val  Ser  His  Ser  Ser  Pro  Ser  Ala  Leu  Ala  Leu  Gln
                    805                     810                     815

Ser  Pro  Leu  Leu  Pro  Ala  Trp  Arg  Thr  Leu  Ser  Val  Ser  Glu  His  Ala
               820                     825                     830

Pro  Gly  Leu  Pro  Gly  Leu  Pro  Ser  Thr  Ala  Ala  Glu  Val  Glu  Ala  Gln
          835                     840                     845

Arg  Glu  His  Gln  Ala  Ala  Lys  Arg  Ala  Cys  Ser  Ala  Cys  Ala  Gly  Thr
     850                     855                     860

Phe  Gly  Glu  Asp  Thr  Ser  Ala  Leu  Pro  Ala  Pro  Gly  Gly  Gly  Gly  Ser
865                     870                     875                          880

Gly  Gly  Asp  Pro  Thr
               885
```

( 2 ) INFORMATION FOR SEQ ID NO:34:

( i ) SEQUENCE CHARACTERISTICS:

( A ) LENGTH: 564 amino acids
( B ) TYPE: amino acid
( D ) TOPOLOGY: unknown ( x i ) SEQUENCE DESCRIPTION: SEQ ID NO:34:

| Met | Lys | Glu | His | Gly | Gly | Thr | Phe | Ser | Ser | Thr | Gly | Ile | Ser | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Gly | Asp | Ser | Ala | Met | Asp | Ser | Leu | Gln | Pro | Leu | Gln | Pro | Asn | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Met | Pro | Val | Cys | Leu | Phe | Ala | Glu | Glu | Ser | Tyr | Gln | Lys | Leu | Ala | Met |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Glu | Thr | Leu | Glu | Glu | Leu | Asp | Trp | Cys | Leu | Asp | Gln | Leu | Glu | Thr | Ile |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Thr | Tyr | Arg | Ser | Val | Ser | Glu | Met | Ala | Ser | Asn | Lys | Phe | Lys | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Met | Leu | Asn | Arg | Glu | Leu | Thr | His | Leu | Ser | Glu | Met | Ser | Arg | Ser | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Gln | Val | Ser | Glu | Val | Ile | Ser | Asn | Thr | Phe | Leu | Asp | Lys | Gln | Asn |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Asp | Val | Glu | Ile | Pro | Ser | Pro | Thr | Gln | Lys | Asp | Arg | Glu | Lys | Lys | Lys |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Lys | Gln | Gln | Leu | Met | Thr | Gln | Ile | Ser | Gly | Val | Lys | Lys | Leu | Met | His |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Ser | Ser | Leu | Asn | Asn | Thr | Ser | Ile | Ser | Arg | Phe | Gly | Val | Asn | Thr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Glu | Asn | Glu | Asp | His | Leu | Ala | Lys | Glu | Leu | Glu | Asp | Leu | Asn | Lys | Trp |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gly | Leu | Asn | Ile | Phe | Asn | Val | Ala | Gly | Tyr | Ser | His | Asn | Arg | Pro | Leu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Thr | Cys | Ile | Met | Tyr | Ala | Ile | Phe | Gln | Glu | Arg | Asp | Leu | Leu | Lys | Thr |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Phe | Arg | Ile | Ser | Ser | Asp | Thr | Phe | Ile | Thr | Tyr | Met | Met | Thr | Leu | Glu |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Asp | His | Tyr | His | Ser | Asp | Val | Ala | Tyr | His | Asn | Ser | Leu | His | Ala | Ala |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Asp | Val | Ala | Gln | Ser | Thr | His | Val | Leu | Leu | Ser | Thr | Pro | Ala | Leu | Asp |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ala | Val | Phe | Thr | Asp | Leu | Glu | Ile | Leu | Ala | Ala | Ile | Phe | Ala | Ala | Ala |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ile | His | Asp | Val | Asp | His | Pro | Gly | Val | Ser | Asn | Gln | Phe | Leu | Ile | Asn |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Thr | Asn | Ser | Glu | Leu | Ala | Leu | Met | Tyr | Asn | Asp | Glu | Ser | Val | Leu | Glu |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Asn | His | His | Leu | Ala | Val | Gly | Phe | Lys | Leu | Leu | Gln | Glu | Glu | His | Cys |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Asp | Ile | Phe | Met | Asn | Leu | Thr | Lys | Lys | Gln | Arg | Gln | Thr | Leu | Arg | Lys |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Met | Val | Ile | Asp | Met | Val | Leu | Ala | Thr | Asp | Met | Ser | Lys | His | Met | Ser |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Leu | Leu | Ala | Asp | Leu | Lys | Thr | Met | Val | Glu | Thr | Lys | Lys | Val | Thr | Ser |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Ser | Gly | Val | Leu | Leu | Leu | Asp | Asn | Tyr | Thr | Asp | Arg | Ile | Gln | Val | Leu |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Arg | Asn | Met | Val | His | Cys | Ala | Asp | Leu | Ser | Asn | Pro | Thr | Lys | Ser | Leu |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

```
Glu  Leu  Tyr  Arg  Gln  Trp  Thr  Asp  Arg  Ile  Met  Glu  Glu  Phe  Phe  Gln
               405                 410                      415

Gln  Gly  Asp  Lys  Glu  Arg  Glu  Arg  Gly  Met  Glu  Ile  Ser  Pro  Met  Cys
               420                 425                      430

Asp  Lys  His  Thr  Ala  Ser  Val  Glu  Lys  Ser  Gln  Val  Gly  Phe  Ile  Asp
               435                 440                      445

Tyr  Ile  Val  His  Pro  Leu  Trp  Glu  Thr  Trp  Ala  Asp  Leu  Val  Gln  Pro
               450                 455                      460

Asp  Ala  Gln  Asp  Ile  Leu  Asp  Thr  Leu  Glu  Asp  Asn  Arg  Asn  Trp  Tyr
465                      470                 475                           480

Gln  Ser  Met  Ile  Pro  Gln  Ser  Pro  Ser  Pro  Pro  Leu  Asp  Glu  Gln  Asn
               485                 490                      495

Arg  Asp  Cys  Gln  Gly  Leu  Met  Glu  Lys  Phe  Gln  Phe  Glu  Leu  Thr  Leu
               500                 505                      510

Asp  Glu  Glu  Asp  Ser  Glu  Gly  Pro  Glu  Lys  Glu  Gly  Glu  Gly  His  Ser
               515                 520                      525

Tyr  Phe  Ser  Ser  Thr  Lys  Thr  Leu  Cys  Val  Ile  Asp  Pro  Glu  Asn  Arg
               530                 535                      540

Asp  Ser  Leu  Gly  Glu  Thr  Asp  Ile  Asp  Ile  Ala  Thr  Glu  Asp  Lys  Ser
545                      550                 555                           560

Pro  Val  Asp  Thr
```

( 2 ) INFORMATION FOR SEQ ID NO:35:

( i ) SEQUENCE CHARACTERISTICS:
        ( A ) LENGTH: 673 amino acids
        ( B ) TYPE: amino acid
        ( D ) TOPOLOGY: unknown ( x i ) SEQUENCE DESCRIPTION: SEQ ID NO:35:

```
Met  Met  His  Val  Asn  Asn  Phe  Pro  Phe  Arg  Arg  His  Ser  Trp  Ile  Cys
1                        5                   10                           15

Phe  Asp  Val  Asp  Asn  Gly  Thr  Ser  Ala  Gly  Arg  Ser  Pro  Leu  Asp  Pro
               20                  25                       30

Met  Thr  Ser  Pro  Gly  Ser  Gly  Leu  Ile  Leu  Gln  Ala  Asn  Phe  Val  His
               35                  40                       45

Ser  Gln  Arg  Arg  Glu  Ser  Phe  Leu  Tyr  Arg  Ser  Asp  Ser  Asp  Tyr  Asp
       50                       55                   60

Leu  Ser  Pro  Lys  Ser  Met  Ser  Arg  Asn  Ser  Ser  Ile  Ala  Ser  Asp  Ile
65                       70                  75                           80

His  Gly  Asp  Asp  Leu  Ile  Val  Thr  Pro  Phe  Ala  Gln  Val  Leu  Ala  Ser
               85                  90                       95

Leu  Arg  Thr  Val  Arg  Asn  Asn  Phe  Ala  Ala  Leu  Thr  Asn  Leu  Gln  Asp
               100                 105                      110

Arg  Ala  Pro  Ser  Lys  Arg  Ser  Pro  Met  Cys  Asn  Gln  Pro  Ser  Ile  Asn
               115                 120                      125

Lys  Ala  Thr  Ile  Thr  Glu  Glu  Ala  Tyr  Gln  Lys  Leu  Ala  Ser  Glu  Thr
               130                 135                      140

Leu  Glu  Glu  Leu  Asp  Trp  Cys  Leu  Asp  Gln  Leu  Glu  Thr  Leu  Gln  Thr
145                      150                 155                          160

Arg  His  Ser  Val  Ser  Glu  Met  Ala  Ser  Asn  Lys  Phe  Lys  Arg  Met  Leu
               165                 170                      175

Asn  Arg  Glu  Leu  Thr  His  Leu  Ser  Glu  Met  Ser  Arg  Ser  Gly  Asn  Gln
               180                 185                      190

Val  Ser  Glu  Phe  Ile  Ser  Asn  Thr  Phe  Leu  Asp  Lys  Gln  His  Glu  Val
```

-continued

|  |  |  | 195 |  |  |  | 200 |  |  |  | 205 |  |  |
|---|---|---|---|---|---|---|---|---|---|---|---|---|---|
| Glu | Ile<br>210 | Pro | Ser | Pro | Thr | Gln<br>215 | Lys | Glu | Lys | Glu<br>220 | Lys | Lys | Arg Pro |
| Met<br>225 | Ser | Gln | Ile | Ser | Gly<br>230 | Val | Lys | Lys | Leu | Met<br>235 | His | Ser | Ser Ser Leu<br>240 |
| Thr | Asn | Ser | Ser | Ile<br>245 | Pro | Arg | Phe | Gly | Val<br>250 | Lys | Thr | Gln | Glu Asp<br>255 |
| Val | Leu | Ala | Lys<br>260 | Glu | Leu | Glu | Asp | Val<br>265 | Asn | Lys | Trp | Gly<br>270 | Leu His Val |
| Phe | Arg | Ile<br>275 | Ala | Glu | Leu | Ser | Gly<br>280 | Asn | Arg | Pro | Leu | Thr<br>285 | Val Ile Met |
| His | Thr<br>290 | Ile | Phe | Gln | Glu | Arg<br>295 | Asp | Leu | Leu | Lys | Thr<br>300 | Phe | Lys Ile Pro |
| Val<br>305 | Asp | Thr | Leu | Ile | Thr<br>310 | Tyr | Leu | Met | Thr | Leu<br>315 | Glu | Asp | His Tyr His<br>320 |
| Ala | Asp | Val | Ala | Tyr<br>325 | His | Asn | Asn | Ile | His<br>330 | Ala | Ala | Asp | Val Val Gln<br>335 |
| Ser | Thr | His | Val<br>340 | Leu | Leu | Ser | Thr | Pro<br>345 | Ala | Leu | Glu | Ala<br>350 | Val Phe Thr |
| Asp | Leu | Glu<br>355 | Ile | Leu | Ala | Ala | Ile<br>360 | Phe | Ala | Ser | Ala | Ile<br>365 | His Asp Val |
| Asp | His<br>370 | Pro | Gly | Val | Ser | Asn<br>375 | Gln | Phe | Leu | Ile | Asn<br>380 | Thr | Asn Ser Glu |
| Leu<br>385 | Ala | Leu | Met | Tyr | Asn<br>390 | Asp | Ser | Ser | Val | Leu<br>395 | Glu | Asn | His His Leu<br>400 |
| Ala | Val | Gly | Phe | Lys<br>405 | Leu | Leu | Gln | Glu | Glu<br>410 | Asn | Cys | Asp | Ile Phe Gln<br>415 |
| Asn | Leu | Thr | Lys<br>420 | Lys | Gln | Arg | Gln | Ser<br>425 | Leu | Arg | Lys | Met | Val Ile Asp<br>430 |
| Ile | Val | Leu | Ala<br>435 | Thr | Asp | Met | Ser<br>440 | Lys | His | Met | Asn | Leu<br>445 | Leu Ala Asp |
| Leu | Lys<br>450 | Thr | Met | Val | Glu | Thr<br>455 | Lys | Lys | Val | Thr | Ser<br>460 | Ser | Gly Val Leu |
| Leu<br>465 | Leu | Asp | Asn | Tyr | Ser<br>470 | Asp | Arg | Ile | Gln | Val<br>475 | Leu | Gln | Asn Met Val<br>480 |
| His | Cys | Ala | Asp | Leu<br>485 | Ser | Asn | Pro | Thr | Lys<br>490 | Pro | Leu | Gln | Leu Tyr Arg<br>495 |
| Gln | Trp | Thr | Asp<br>500 | Arg | Ile | Met | Glu | Glu<br>505 | Phe | Phe | Arg | Gln | Gly Asp Arg<br>510 |
| Glu | Arg | Glu<br>515 | Arg | Gly | Met | Glu | Ile<br>520 | Ser | Pro | Met | Cys | Asp<br>525 | Lys His Asn |
| Ala | Ser<br>530 | Val | Glu | Lys | Ser | Gln<br>535 | Val | Gly | Phe | Ile | Asp<br>540 | Tyr | Ile Val His |
| Pro<br>545 | Leu | Trp | Glu | Thr | Trp<br>550 | Ala | Asp | Leu | Val | His<br>555 | Pro | Asp | Ala Gln Asp<br>560 |
| Ile | Leu | Asp | Thr | Leu<br>565 | Glu | Asp | Asn | Arg | Glu<br>570 | Trp | Tyr | Gln | Ser Thr Ile<br>575 |
| Pro | Gln | Ser | Pro<br>580 | Ser | Pro | Ala | Pro | Asp<br>585 | Asp | Pro | Glu | Glu<br>590 | Gly Arg Gln |
| Gly | Gln | Thr<br>595 | Gly | Lys | Phe | Gln | Phe<br>600 | Glu | Leu | Thr | Leu<br>605 | Glu | Glu Asp Gly |
| Glu | Ser<br>610 | Asp | Thr | Glu | Lys | Asp<br>615 | Ser | Gly | Ser | Gln | Val<br>620 | Glu | Glu Asp Thr |

```
Ser  Cys  Ser  Asp  Ser  Lys  Thr  Leu  Cys  Thr  Gln  Asp  Ser  Glu  Ser  Thr
625            630                 635                 640

Glu  Ile  Pro  Leu  Asp  Glu  Gln  Val  Glu  Glu  Ala  Val  Gly  Glu  Glu
               645                 650                 655

Glu  Glu  Ser  Gln  Pro  Glu  Ala  Cys  Val  Ile  Asp  Asp  Arg  Ser  Pro  Asp
               660                 665                 670

Thr
```

( 2 ) INFORMATION FOR SEQ ID NO:36:

( i ) SEQUENCE CHARACTERISTICS:
        ( A ) LENGTH: 336 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:36:

```
GCT  GTC  CAG  AAA  AGG  TCC  CGC  GCA  GTC  GGC  GCT  CGG  TCC  AGC  CTC  CAC    48
Ala  Val  Gln  Lys  Arg  Ser  Arg  Ala  Val  Gly  Ala  Arg  Ser  Ser  Leu  His
               5                        10                      15

GCA  GTC  CTG  GCG  ATG  CAG  GGC  CCC  CCC  GCG  CCC  GCC  CCG  GTC  CCC  GGG    96
Ala  Val  Leu  Ala  Met  Gln  Gly  Pro  Pro  Ala  Pro  Ala  Pro  Val  Pro  Gly
               20                       25                      30

CCC  GGC  TCC  CCT  CGG  GGA  TCC  CCG  CGC  GGC  TCC  CCC  GGG  CTC  TTC  AGG   144
Pro  Gly  Ser  Pro  Arg  Gly  Ser  Pro  Arg  Gly  Ser  Pro  Gly  Leu  Phe  Arg
               35                       40                      45

AAG  CTT  TTG  GTG  AAT  CAG  AGC  ATC  CGC  CTG  CAG  CGG  CGC  TTC  ACG  GTG   192
Lys  Leu  Leu  Val  Asn  Gln  Ser  Ile  Arg  Leu  Gln  Arg  Arg  Phe  Thr  Val
               50                       55                      60

GCC  CAT  CCG  CTG  TGC  TTT  GAC  CTG  GAA  AAT  GGG  CTC  TCG  TGT  GGG  AGG   240
Ala  His  Pro  Leu  Cys  Phe  Asp  Leu  Glu  Asn  Gly  Leu  Ser  Cys  Gly  Arg
65                      70                       75                      80

AGG  GCC  CTG  GAC  CCT  CAG  TCC  AGC  CCT  GGC  CTG  GGC  CGG  ATT  ATG  CAG   288
Arg  Ala  Leu  Asp  Pro  Gln  Ser  Ser  Pro  Gly  Leu  Gly  Arg  Ile  Met  Gln
               85                       90                      95

GCT  CCA  GTC  CCG  CAC  AGC  CAG  CGG  CGC  GAG  TCC  TTC  CTG  TAC  CGC  TCA   336
Ala  Pro  Val  Pro  His  Ser  Gln  Arg  Arg  Glu  Ser  Phe  Leu  Tyr  Arg  Ser
               100                      105                     110
```

( 2 ) INFORMATION FOR SEQ ID NO:37:

( i ) SEQUENCE CHARACTERISTICS:
        ( A ) LENGTH: 112 amino acids
        ( B ) TYPE: amino acid
        ( D ) TOPOLOGY: unknown ( x i ) SEQUENCE DESCRIPTION: SEQ ID NO:37:

```
Ala  Val  Gln  Lys  Arg  Ser  Arg  Ala  Val  Gly  Ala  Arg  Ser  Ser  Leu  His
1               5                        10                      15

Ala  Val  Leu  Ala  Met  Gln  Gly  Pro  Pro  Ala  Pro  Ala  Pro  Val  Pro  Gly
               20                        25                      30

Pro  Gly  Ser  Pro  Arg  Gly  Ser  Pro  Arg  Gly  Ser  Pro  Gly  Leu  Phe  Arg
               35                        40                      45

Lys  Leu  Leu  Val  Asn  Gln  Ser  Ile  Arg  Leu  Gln  Arg  Arg  Phe  Thr  Val
               50                        55                      60

Ala  His  Pro  Leu  Cys  Phe  Asp  Leu  Glu  Asn  Gly  Leu  Ser  Cys  Gly  Arg
65                       70                       75                      80

Arg  Ala  Leu  Asp  Pro  Gln  Ser  Ser  Pro  Gly  Leu  Gly  Arg  Ile  Met  Gln
               85                        90                      95

Ala  Pro  Val  Pro  His  Ser  Gln  Arg  Arg  Glu  Ser  Phe  Leu  Tyr  Arg  Ser
               100                       105                     110
```

( 2 ) INFORMATION FOR SEQ ID NO:38:

( i ) SEQUENCE CHARACTERISTICS:
        ( A ) LENGTH: 438 amino acids
        ( B ) TYPE: amino acid
        ( D ) TOPOLOGY: unknown ( x i ) SEQUENCE DESCRIPTION: SEQ ID NO:38:

```
Glu  Thr  Leu  Glu  Glu  Leu  Asp  Trp  Cys  Leu  Glu  Gln  Leu  Glu  Thr  Leu
 1              5                        10                       15
Gln  Thr  Arg  Arg  Ser  Val  Gly  Glu  Met  Ala  Ser  Asn  Lys  Phe  Lys  Arg
              20                        25                       30
Met  Leu  Asn  Arg  Glu  Leu  Thr  His  Leu  Ser  Glu  Thr  Ser  Arg  Ser  Gly
              35                        40                       45
Asn  Gln  Val  Ser  Glu  Tyr  Ile  Ser  Gln  Thr  Phe  Leu  Asp  Gln  Gln  Ala
         50                   55                       60
Glu  Val  Glu  Leu  Pro  Ala  Leu  Arg  Lys  Ser  Cys  His  Thr  Thr  Ala  Ala
 65                       70                   75                            80
Ile  Pro  Arg  Phe  Gly  Val  Gln  Thr  Asp  Gln  Glu  Glu  Gln  Leu  Ala  Lys
                   85                        90                       95
Glu  Leu  Glu  Asp  Thr  Asn  Lys  Trp  Gly  Leu  Asp  Val  Phe  Lys  Val  Ala
              100                       105                      110
Glu  Leu  Ser  Gly  Asn  Arg  Pro  Leu  Thr  Ala  Val  Ile  Phe  Arg  Val  Leu
              115                       120                      125
Gln  Glu  Arg  Asp  Leu  Leu  Lys  Thr  Phe  Gln  Ile  Pro  Ala  Asp  Thr  Leu
              130                       135                      140
Leu  Arg  Tyr  Leu  Leu  Thr  Leu  Glu  Gly  His  Tyr  His  Ser  Asn  Val  Ala
145                            150                      155                  160
Tyr  His  Asn  Ser  Ile  His  Ala  Ala  Asp  Val  Val  Gln  Ser  Ala  His  Val
                   165                       170                      175
Leu  Leu  Gly  Thr  Pro  Ala  Leu  Glu  Ala  Val  Phe  Thr  Asp  Leu  Glu  Val
              180                       185                      190
Leu  Ala  Ala  Ile  Phe  Ala  Cys  Ala  Ile  His  Asp  Val  Asp  His  Pro  Gly
              195                       200                      205
Val  Ser  Asn  Gln  Phe  Leu  Ile  Asn  Thr  Asn  Ser  Glu  Leu  Ala  Leu  Met
         210                  215                       220
Tyr  Asn  Asp  Ser  Ser  Val  Leu  Glu  Asn  His  His  Leu  Ala  Val  Gly  Phe
225                       230                       235                      240
Lys  Leu  Leu  Gln  Gly  Glu  Asn  Cys  Asp  Ile  Phe  Gln  Asn  Leu  Ser  Thr
                   245                       250                      255
Lys  Gln  Lys  Leu  Ser  Leu  Arg  Arg  Met  Val  Ile  Asp  Met  Val  Leu  Ala
              260                       265                      270
Thr  Asp  Met  Ser  Lys  His  Met  Ser  Leu  Leu  Ala  Asp  Leu  Lys  Thr  Met
              275                       280                      285
Val  Glu  Thr  Lys  Lys  Val  Thr  Ser  Leu  Gly  Val  Leu  Leu  Leu  Asp  Asn
         290                  295                       300
Tyr  Ser  Asp  Arg  Ile  Gln  Val  Leu  Gln  Ser  Leu  Val  His  Cys  Ala  Asp
305                       310                       315                      320
Leu  Ser  Asn  Pro  Ala  Lys  Pro  Leu  Pro  Leu  Tyr  Arg  Gln  Trp  Thr  Glu
                   325                       330                      335
Arg  Ile  Met  Ala  Glu  Phe  Phe  Gln  Gln  Gly  Asp  Arg  Glu  Arg  Glu  Ser
              340                       345                      350
Gly  Leu  Asp  Ile  Ser  Pro  Met  Cys  Asp  Lys  His  Thr  Ala  Ser  Val  Glu
              355                       360                      365
```

```
Lys  Ser  Gln  Val  Gly  Phe  Ile  Asp  Tyr  Ile  Ala  His  Pro  Leu  Trp  Glu
     370                 375                      380

Thr  Trp  Ala  Asp  Leu  Val  His  Pro  Asp  Ala  Gln  Glu  Leu  Leu  Asp  Thr
385                      390                 395                           400

Leu  Glu  Asp  Asn  Arg  Glu  Trp  Tyr  Gln  Ser  Arg  Val  Pro  Pro  Glu  Arg
                    405                 410                      415

Asp  Gly  Pro  Asp  Arg  Phe  Gln  Phe  Glu  Leu  Thr  Leu  Glu  Glu  Ala  Glu
               420                 425                      430

Glu  Glu  Asp  Glu  Glu  Glu
               435
```

(2) INFORMATION FOR SEQ ID NO:39:

(i) SEQUENCE CHARACTERISTICS:
        (A) LENGTH: 10 amino acids
        (B) TYPE: amino acid
        (D) TOPOLOGY: unknown (xi) SEQUENCE DESCRIPTION: SEQ ID NO:39:

```
Met  Glu  Thr  Leu  Glu  Glu  Leu  Asp  Trp  Cys
  1            5                           10
```

(2) INFORMATION FOR SEQ ID NO:40:

(i) SEQUENCE CHARACTERISTICS:
        (A) LENGTH: 501 amino acids
        (B) TYPE: amino acid
        (D) TOPOLOGY: unknown (xi) SEQUENCE DESCRIPTION: SEQ ID NO:40:

```
Glu  Thr  Leu  Glu  Glu  Leu  Asp  Trp  Cys  Leu  Asp  Gln  Leu  Glu  Thr  Leu
  1                 5                      10                           15

Gln  Thr  Arg  His  Ser  Val  Gly  Glu  Met  Ala  Ser  Asn  Lys  Phe  Lys  Arg
               20                      25                      30

Ile  Leu  Asn  Arg  Glu  Leu  Thr  His  Leu  Ser  Glu  Thr  Ser  Arg  Ser  Gly
               35                      40                      45

Asn  Gln  Val  Ser  Glu  Tyr  Ile  Ser  Arg  Thr  Phe  Leu  Asp  Gln  Gln  Thr
     50                      55                           60

Glu  Val  Glu  Leu  Pro  Lys  Val  Thr  Ala  Glu  Glu  Ala  Pro  Gln  Pro  Met
 65                      70                      75                           80

Ser  Arg  Ile  Ser  Gly  Leu  His  Gly  Leu  Cys  His  Ser  Ser  Ala  Thr  Val
                    85                      90                           95

Pro  Arg  Phe  Gly  Val  Gln  Thr  Asp  Gln  Glu  Gln  Leu  Ala  Lys  Glu
               100                     105                     110

Leu  Glu  Asp  Thr  Asn  Lys  Trp  Gly  Leu  Asp  Val  Phe  Lys  Val  Ala  Glu
               115                     120                     125

Leu  Ser  Gly  Asn  Gln  Pro  Leu  Thr  Ala  Ile  Ile  Phe  Ser  Ile  Phe  Gln
     130                     135                     140

Glu  Arg  Asp  Leu  Leu  Lys  Thr  Phe  Gln  Ile  Pro  Ala  Asp  Thr  Leu  Ala
145                          150                     155                     160

Thr  Tyr  Leu  Leu  Met  Leu  Glu  Gly  His  Tyr  His  Ala  Asn  Val  Ala  Tyr
                    165                     170                          175

His  Asn  Ser  Leu  His  Ala  Ala  Asp  Val  Ala  Gln  Ser  Thr  His  Val  Leu
               180                     185                     190

Leu  Ala  Thr  Pro  Ala  Leu  Glu  Ala  Val  Phe  Thr  Asp  Leu  Glu  Ile  Leu
          195                     200                     205

Ala  Ala  Leu  Phe  Ala  Ser  Ala  Ile  His  Asp  Val  Asp  His  Pro  Gly  Val
     210                     215                     220
```

-continued

```
Ser Asn Gln Phe Leu Ile Asn Thr Asn Ser Glu Leu Ala Leu Met Tyr
225             230             235                         240

Asn Asp Ala Ser Val Leu Glu Asn His His Leu Ala Val Gly Phe Lys
                245             250                     255

Leu Leu Gln Ala Glu Asn Cys Asp Ile Phe Gln Asn Leu Ser Ala Lys
            260             265                     270

Gln Arg Leu Ser Leu Arg Arg Met Val Ile Asp Met Val Leu Ala Thr
        275             280             285

Asp Met Ser Lys His Met Asn Leu Leu Ala Asp Leu Lys Thr Met Val
    290             295             300

Glu Thr Lys Lys Val Thr Ser Leu Gly Val Leu Leu Leu Asp Asn Tyr
305             310             315                         320

Ser Asp Arg Ile Gln Val Leu Gln Asn Leu Val His Cys Ala Asp Leu
            325             330                     335

Ser Asn Pro Thr Lys Pro Leu Pro Leu Tyr Arg Gln Trp Thr Asp Arg
            340             345                 350

Ile Met Ala Glu Phe Phe Gln Gln Gly Asp Arg Glu Arg Glu Ser Gly
        355             360             365

Leu Asp Ile Ser Pro Met Cys Asp Lys His Thr Ala Ser Val Glu Lys
    370             375             380

Ser Gln Val Gly Phe Ile Asp Tyr Ile Ala His Pro Leu Trp Glu Thr
385             390             395                         400

Trp Ala Asp Leu Val His Pro Asp Ala Gln Asp Leu Leu Asp Thr Leu
            405             410             415

Glu Asp Asn Arg Glu Trp Tyr Gln Ser Lys Ile Pro Arg Ser Pro Ser
            420             425             430

Asp Leu Thr Asn Pro Glu Arg Asp Gly Pro Asp Arg Phe Gln Phe Glu
        435             440             445

Leu Thr Leu Glu Glu Ala Glu Glu Glu Asp Glu Glu Glu Glu Glu Glu
    450             455             460

Gly Glu Glu Thr Ala Leu Ala Lys Glu Ala Leu Glu Leu Pro Asp Thr
465             470             475             480

Glu Leu Leu Ser Pro Glu Ala Gly Pro Ala Pro Gly Asp Leu Pro Leu
            485             490                     495

Asp Asn Gln Arg Thr
            500
```